United States Patent
Wieland

(10) Patent No.: US 12,234,484 B2
(45) Date of Patent: Feb. 25, 2025

(54) CULTURE MEDIUM FOR PLURIPOTENT STEM CELLS

(71) Applicant: PROMOCELL GMBH, Heidelberg (DE)

(72) Inventor: Hagen Wieland, Heidelberg (DE)

(73) Assignee: PROMOCELL GMBH, Heidelberg (DE)

(*) Notice: Subject to any disclaimer, the term of this patent is extended or adjusted under 35 U.S.C. 154(b) by 12 days.

(21) Appl. No.: 16/096,806

(22) PCT Filed: May 18, 2018

(86) PCT No.: PCT/EP2018/063036
§ 371 (c)(1),
(2) Date: Oct. 26, 2018

(87) PCT Pub. No.: WO2018/219684
PCT Pub. Date: Dec. 6, 2018

(65) Prior Publication Data
US 2020/0332263 A1 Oct. 22, 2020

(30) Foreign Application Priority Data
May 31, 2017 (EP) .................................... 17173816

(51) Int. Cl.
*C12N 5/074* (2010.01)
(52) U.S. Cl.
CPC ........ *C12N 5/0696* (2013.01); *C12N 2500/05* (2013.01); *C12N 2500/30* (2013.01); *C12N 2500/36* (2013.01); *C12N 2500/38* (2013.01); *C12N 2500/98* (2013.01); *C12N 2501/15* (2013.01); *C12N 2501/16* (2013.01); *C12N 2501/999* (2013.01); *C12N 2533/90* (2013.01)

(58) Field of Classification Search
None
See application file for complete search history.

(56) References Cited

U.S. PATENT DOCUMENTS

| | | | | |
|---|---|---|---|---|
| 2010/0035859 A1* | 2/2010 | Wilson | ..................... | A61P 25/16 514/211.13 |
| 2015/0175956 A1* | 6/2015 | Elhofy | .................. | A01N 1/0226 435/404 |
| 2015/0329832 A1* | 11/2015 | Senda | ................... | C12N 5/0696 435/377 |

OTHER PUBLICATIONS

Yao et al (Reproductive Medicine and Biology, 16: 99-117, 2017 (Year: 2017).*
Xiao (Stem Cells, 24(1): 1476-1486, 2005) (Year: 2005).*
Kornhuber et al (Cellular Physiology and Biochemistry, 26(1): 9-20, 2010 (Year: 2010).*
Valuer et al (Journal of Cell Science, 118(19): 4495-4509, 2005) (Year: 2005).*
Kumagai et al (BBRC, 434(4): 710-716, 2013 (Year: 2013).*
Vallier (Journal of Cell Science, 118: 4495-4509, 2005 (Year: 2005).*
Kumagai (Biochemical and Biophysical Research Communications, 434: 710-716, 2013 (Year: 2013).*
Chen (Nat Methods, 8(5): 1-22, 2011 (Year: 2011).*
Kornhuber (Cell Physiol Biochem, 26: 1-12, 2010). (Year: 2010).*
Meng (abstract 2010 (Year: 2010).*
Fan (Stem Cell Rev, 11(1): 96-109, 2015), (Year: 2015).*
Millipore Sigma "Iscove's Modified Dulbecco's Media (IMDM) Formulation", available online, Iscove's Modified Dulbecco's Media (IMDM) Formulation (sigmaaldrich.com), accessed Apr. 22, 2023, copyright 2023 (Year: 2023).*
Arora, Meenakshi. "Cell culture media: a review." Mater Methods 3.175 (2013): 24. (Year: 2013).*
Vallier et al., "Activin/Nodal and FGF pathways cooperate to maintain pluripotency of human embryonic stem cells", Journal of Cell Science, 118(19): 4495-4509 (2005).
Kumagai et al., "Identification of small molecules that promote human embryonic stem cell self-renewal", Biochemical and Biophysical Research Communications, 434(4): 710-716 (2013).
Fan et al., "Production of Human Pluripotent Stem Cell Therapeutics under Defined Xeno-free Conditions: Progress and Challenges", Stem Cell Rev and Rep 11(1): 96-109 (2014).
Xiao et al., "Activin A Maintains Self-Renewal and Regulates Fibroblast Growth Factor, Wnt, and Bone Morphogenic Protein Pathways in Human Embryonic Stem Cells", Stem Cells, 24: 1476-1486 (2006).
Desbordes et al., "High-Throughput Screening Assay for the Identification of Compounds Regulating Self-Renewal and Differentiation in Human Embryonic Stem Cells", Cell Stem Cell, 2(6): 602-612 (2008).
Zhang et al., "Small molecules, big roles—the chemical manipulation of stem cell fate and somatic cell reprogramming", Journal of Cell Science, 125(23): 5609-5620 (2012).
Kornhuber et al., "Functional Inhibitors of Acid Sphingomyelinase (FIASMAs): A Novel Pharmacological Group of Drugs with Broad Clinical Applications", Cellular Physiology and Biochemistry, 26(1): 9-20 (2010).
International Search Report, issued Jul. 6, 2018 in corresponding International Patent Application No. PCT/EP2018/063036.

* cited by examiner

Primary Examiner — Emily A Cordas
(74) Attorney, Agent, or Firm — Wenderoth, Lind & Ponack, L.L.P.

(57) ABSTRACT

The present invention relates to a chemically defined medium for eukaryotic cell culture, comprising water, at least one carbon source, one or more vitamins, one or more salts, one or more fatty acids, one or more buffer components, selenium, at least one substance of the group of Functional Inhibitors of Acid Sphingomyelinase (FIASMAs) and at least one polypeptide of the TGF-β superfamily with the ability to inhibit stem cell differentiation, its use in the culture of human pluripotent stem cells, a cell culture system comprising human pluripotent stem cells and the chemically defined medium, as well as a kit for proliferation and/or maintenance of human pluripotent stem cells.

18 Claims, 6 Drawing Sheets

CULTURE MEDIUM FOR PLURIPOTENT STEM CELLS

FIELD OF THE INVENTION

Figure 1:
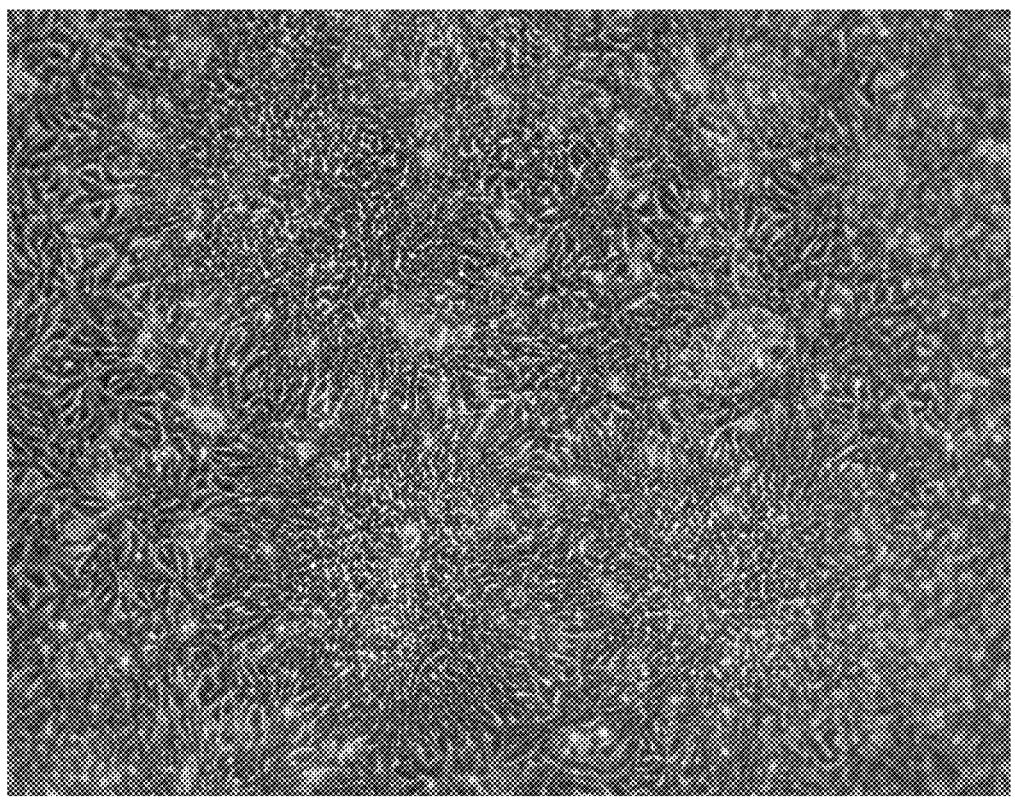

The present invention relates to a chemically defined medium for eukaryotic cell culture, the use of the medium for the proliferation and/or maintenance of pluripotent stem cells, a cell culture system comprising pluripotent stem cells and the chemically defined medium, as well as a kit for proliferation and/or maintenance of pluripotent stem cells.

BACKGROUND OF THE INVENTION

Self-renewal and the ability to differentiate into various terminally mature cell types are the hallmarks shared by all types of stem cells. These mechanisms are tightly controlled in normal stem cells but the potential is progressively lost during the gradual multi-staged differentiation process of stem cells towards terminally differentiated mature cells (Sanges et al., 2010).

The potency of a stem cell specifies its potential to differentiate into different cell types. Stem cells can be classified according to their potency, e.g. totipotent stem cells can differentiate into all cell types, embryonic and extraembryonic. Totipotent stem cells are produced from the fusion of an egg and sperm cell and can construct a complete, viable organism. In contrast, unipotent stem cells can produce only one cell type, but have the property of self-renewal, which distinguishes them from non-stem cells. Types of stem cells that can differentiate in some but not all cell types are multipotent stem cells, which can differentiate into a number of cell types, but only those of a closely related family of cells. Pluripotent stem cells can differentiate into nearly all cells, excluding extra-embryonic tissues, e.g. the placenta (Schöler, 2007).

The two most well-known examples of pluripotent stem cells (PSC) are embryonic stem cells (ESC) and induced pluripotent stem cells (iPS) (Sanges et al., 2010).

Embryonic stem cells were the first type of pluripotent stem cells isolated and taken into culture and were initially derived from the inner cell mass (ICM) of a developing mouse embryo in 1981 (Pauklin et al., 2011). These cells proliferate indefinitely and are genetically stable.

The advent of human embryonic stem cells in 1998 (Thomson et al., 1998), catapulted stem cell research to new heights. Embryonic stem cell research conquered science at a breath-taking pace, leading to major advances in cell and developmental biology (Wobus et al., 2005).

Today, embryonic stem cells derived from various species represent versatile biological tools, e.g. for the directed differentiation into various cell types, gene targeting and generation of transgenic animals (Wobus et al., 2005). Importantly, their unlimited self-renewal capacity in combination with the ability to differentiate into cells with therapeutic value has given rise to new hope for the therapy of many non-treatable medical conditions.

First described in 2006 for the murine system (Takahashi and Yamanaka, 2006) and 2007 in man (Takahashi et al., 2007; Yu et al., 2007), iPS cells are artificially generated by re-programming mature somatic cells back into a pluripotent state. The principle is based on inducing the expression of distinct pluripotency genes by means of various technical approaches (González et al., 2011). This elegant and revolutionary technique allowed for the circumvention of the ethical concerns associated with blastocyst-derived hESC and opened new possibilities for the generation of patient-specific stem cells and disease models. At first glance, iPSC share many features with ESC, e.g. morphology, pluripotency and marker expression. Detailed analysis, however, revealed some fundamental differences between hESC and their artificially generated counterpart, e.g. variance in epigenetic modifications/DNA-methylation ("imprinting") and accumulation of mutations during the somatic stage of the cell (Puri and Nagy, 2012).

It is important to note that pluripotent cell lines can also be established either directly from epiblast cells or indirectly from their unipotent descendants, the primordial germ cells (PGC), by in vitro dedifferentiation into pluripotent embryonic germ cells (EGC).

Additional, yet rarely used techniques to reprogram mature somatic cells back into a pluripotent state are somatic-cell nuclear transfer (SCNT) and cell fusion (Sanges et al., 2010). SCNT achieves the reprogramming process by transfer of a somatic nucleus into an enucleated oocyte. This technique generates a fully functional embryo and is sometimes used for cloning of (transgenic) animals, e.g. "Dolly the sheep" ("reproductive cloning") (Wilmut et al., 1997) but can also be used for the establishment of patient specific pluripotent cell lines ("therapeutic cloning").

Lastly, cell fusion employs the generation of tetraploid or polyploid pluripotent cell hybrids by fusion of a pluripotent stem cell with a somatic cell.

Despite the significant therapeutic potential that pluripotent cells hold, at present science has not reached the threshold required for safe and efficient therapies based on pluripotent cells.

Ironically, the virtually unlimited possibilities of these cells represent the main obstacle for their use in a broad range of therapeutic applications: residual pluripotent cells in cell preparations for transplantation pose a high risk for developing cancer/tumors and there are no safe techniques to guarantee the absence of such dangerous cell impurities at the moment (Puri and Nagy, 2012). In addition, even after 15 years of hESC-culture, overall optimized differentiation protocols that give functionally transplantable cells remain scarce (Bilic and Izpisua Belmonte, 2012).

The pluripotency of PSC can be assessed by various direct and indirect technical approaches. The gold standard for animal cells is the generation of chimeras and testing for contribution to all tissues including germline transmission (Sheridan et al., 2012; Jaenisch and Young, 2008).

For human pluripotent stem cells these rigorous tests for pluripotency cannot be performed for obvious ethical reasons. Therefore, indirect methods (e.g. the formation of teratomas in immunocompromised mice or embryoid bodies with differentiation into all three germ layers) are used as alternative methods of pluripotency testing of human PSC (Sheridan et al., 2012). These approaches are laborious, expensive/time-consuming and technically challenging. As such, testing for pluripotency marker expression patterns, e.g. Oct-3/4, Nanog, SSEA and Tra-antigens is also currently widely accepted as an indirect proof of a pluripotent state (Wenxiu et al., 2012). Indeed, to date no technique is available to ultimately verify the pluripotency of existing hPSC lines by functional means.

Thus, one of the big challenges in stem cell culturing is the maintenance of pluripotency. In the first PSC research, embryonic stem cells were cultured on feeder cell layers, mostly murine embryonic fibroblasts (MEF), in non-defined culture media containing FCS (Wobus et al., 2005). However, the presence of undefined substances in the culture media often led to spontaneous differentiation of the cultured cells resulting in a loss of pluripotency. Later on, FCS could be replaced by somewhat more defined serum replacements. The introduction of extracellular matrix coatings supporting self-renewal of ESC allowed for feeder-free culture using feeder-cell conditioned medium. However, the culture process remained time-consuming, laborious and poorly defined.

In recent years, PSC-culture has experienced significant technical progress. Defined media compositions became a standard, followed by the first xeno-free defined formulations. However, all these culture systems still depended on non-defined, xenogenic and poorly standardized extracellular matrix (ECM) preparations—a contradiction in terms when using defined/xeno-free media. Indeed, research just recently overcame this hurdle and identified natural/synthetic ECM molecules and peptides supporting undifferentiated PSC-expansion. Scientists are now capable of completely defined/humanized derivation and culture of hPSC.

The first established defined and feeder-free in vitro culture systems for human pluripotent stem cells (hPSC) contained FGF-2 (FGFR ligand) and TGFβ-1 (ALK5 ligand) to robustly support their expansion, sustained self-renewal, and maintenance of pluripotency (Ludwig et al., 2006). While FGF-2 or TGFβ-1 on their own are not able to robustly keep hPSC in an undifferentiated state under defined and feeder-free culture conditions, the combined activation of FGF/TGF-signaling can.

However, these media for culturing undifferentiated human stem cells have not been fully developed for large-scale cultures of cells. They are expensive and batch-to-batch variations can occur.

Hence, despite these recent technical advancements, the established hPSC culture systems still share one or more of the following unfavorable properties: use supra-physiologically high amounts of growth factors, contain substances purified from human or animal origin, or rely on animal-derived and/or non-defined ECM.

Ongoing research tries to circumvent these unfavorable properties. Scientific work demonstrated that self-renewal support of hPSC could—at least in part—also be achieved by engagement of alternative signaling pathways like the ErbB3-signaling pathway which as described in U.S. Pat. No. 8,211,699 B2 or Nodal/Activin-signaling (Vallier et al., 2005; Xiao et al., 2006). Activin a, an ActRIIA/ALK4-ligand, is able to extend pluripotency of a limited number of hPSC lines on its own (Xiao et al., 2006), but fails to do so for other established lines (Vallier et al., 2005). In contrast, the combination of activin a with FGF-2 could robustly maintain hPSC in a pluripotent state under these culture conditions (Vallier et al., 2009).

Recent scientific advancements lead to the emergence of small molecules capable of specifically manipulating cellular signaling, e.g. to aid reprogramming of somatic cells in order to generate PS cell lines (Zhang et al., 2012). Some of these organic chemicals also bear potential for supporting maintenance of self-renewal and pluripotency of hPSC in absence of the classical cytokines, e.g. FGF-2 and TGFβ-1.

Different tricyclic antidepressant neurotransmitter-antagonists of the substance class of the dibenzazepines, such as trimipramine, have been demonstrated to specifically extend the pluripotency of certain hPSC lines in the absence of added FGF-2 and defined and feeder-free culture conditions (Kumagai et al., 2013). However, this seemed only to be true for selected hPSC lines but did not apply in general. Other established cell lines exhibited gradual differentiation and could not be propagated in the presence of trimipramine.

Accordingly, it is an object of the present invention to provide an improved chemically defined cell culture medium for culture of a broad spectrum of established pluripotent stem cell lines maintaining pluripotency when continuously passaged using said medium.

SUMMARY OF THE INVENTION

This object is solved by the subject matter of the present invention. The present invention provides a chemically defined medium for eukaryotic cell culture, comprising water, at least one carbon source, one or more vitamins, one or more salts, one or more fatty acids, one or more buffer components, selenium, at least one substance of the group of FIASMAs and at least one polypeptide of the TGF-β superfamily with the ability to inhibit stem cell differentiation.

The present inventors have identified the synergistic effect of a FIASMA in combination with a TGF-β superfamily member within the chemically defined culture medium according to the invention that allows the expansion and maintenance of hPSC in an undifferentiated state in a standardized culture environment. The chemically defined medium according to the invention enables for continuous proliferation and serial passageability of hPSC cultures indicative for the maintenance of hPSC self-renewal. Once the hPSC culture is initiated, cells can be continuously passaged.

The medium formulation is not only chemically defined/xeno-free, but also completely excludes substances purified from human or animal origin. In addition, the medium works with concentrations of the used compounds in the lower physiological range.

The optimal culture environment allows for a well-controlled culture process, consistent and reproducible performance and robust support of pluripotency for established pluripotent stem cell lines.

The present invention further provides the use of the chemically defined medium for culturing eukaryotic cells preferably human pluripotent stem cells, more preferably human induced pluripotent stem cells. Accordingly, the present invention also provides a cell culture system, comprising human pluripotent stem cells, preferably human induced pluripotent stem cells, and the chemically defined medium.

Additionally, the present invention provides a kit for proliferation and/or maintenance of human pluripotent stem cells in cell culture, comprising:
- a first composition comprising an extracellular matrix preparation, preferably a xeno-free extracellular matrix preparation,
- a second composition comprising water, at least one carbon source, one or more vitamins, one or more salts, one or more fatty acids and one or more buffer components,
- a third composition comprising ascorbic acid, selenium, insulin, transferrin, activin a and trimipramine, and
- optionally a fourth composition for dissociation of cells.

FIGURES

FIG. 1 shows a light microscopy image at 50× magnification of hPSC expanded for 1 passage (5 days) in a stem cell culture medium containing 10 µg/L activin a (as defined in Example 4). The cells experienced significant proliferation but exhibited a highly heterogeneous morphological pattern. The cell size drastically increased (low nuclear: cytoplasmic ratio) and large numbers of detached cells were observed between media changes, indicative for significant differentiation and the inability of activin a to maintain the hPSC in an undifferentiated state.

Figure 2:
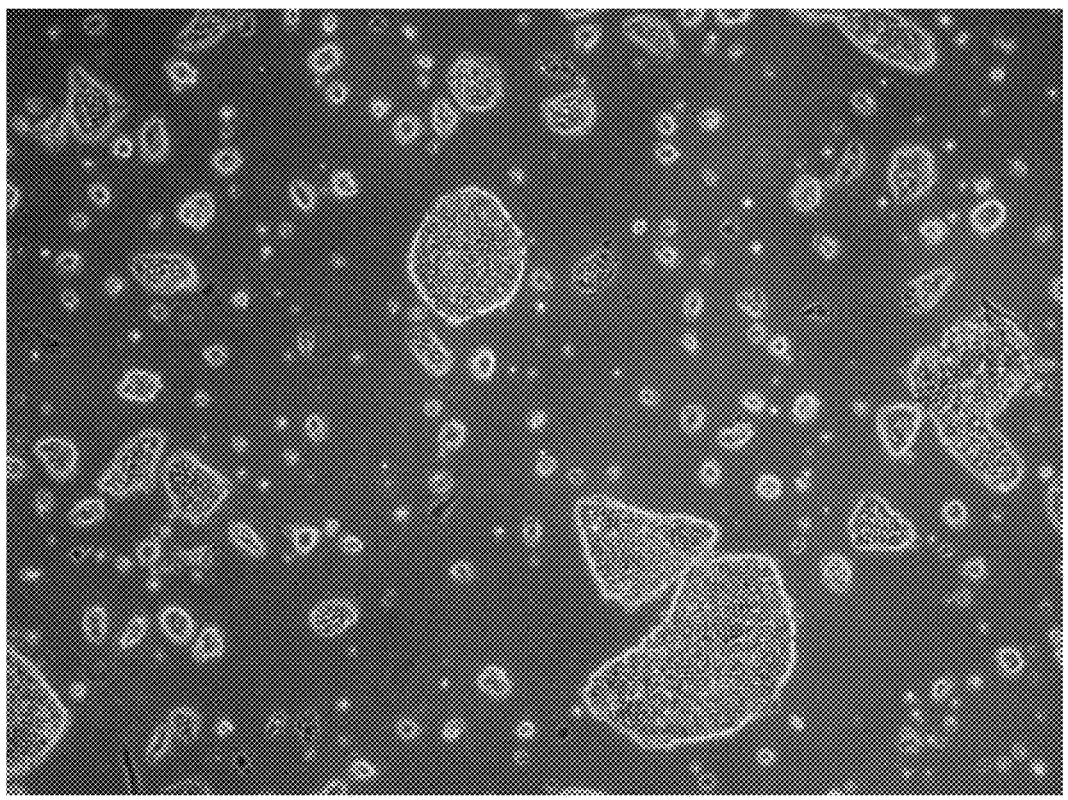

FIG. 2 shows a light microscopy image at 50× magnification of hPSC cultured for 5 days in a stem cell culture medium containing trimipramine (as defined in Example 5). The cells retained a typical pluripotent stem cell phenotype with a high nuclear:cytoplasmic ratio and smooth-edged colonies. However, with trimipramine, the seeded cell clumps remained nearly the same size over the complete culture period, indicative of a complete lack of cell proliferation.

Figure 3:
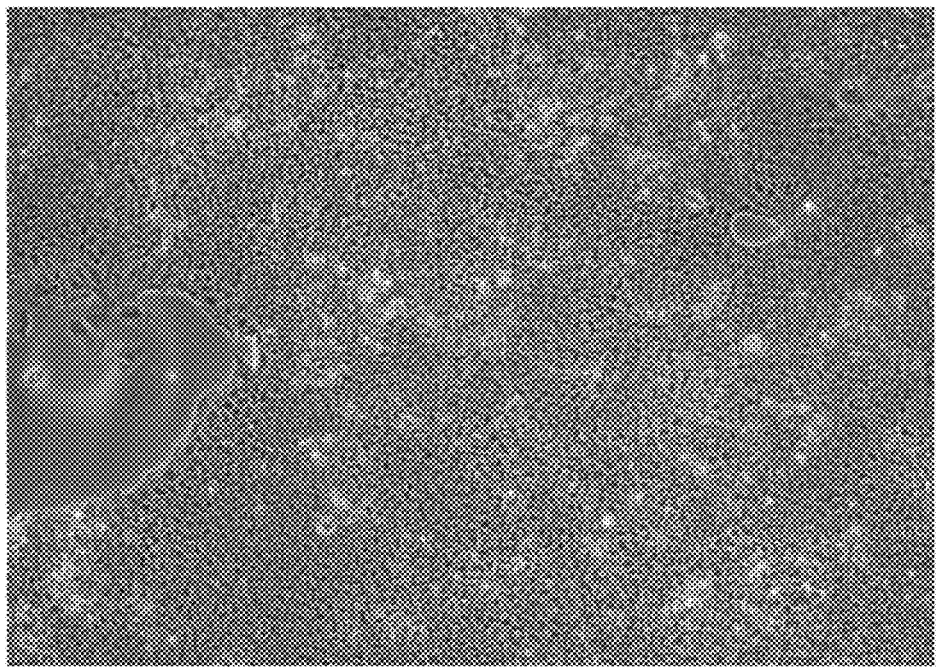
Figure 3:
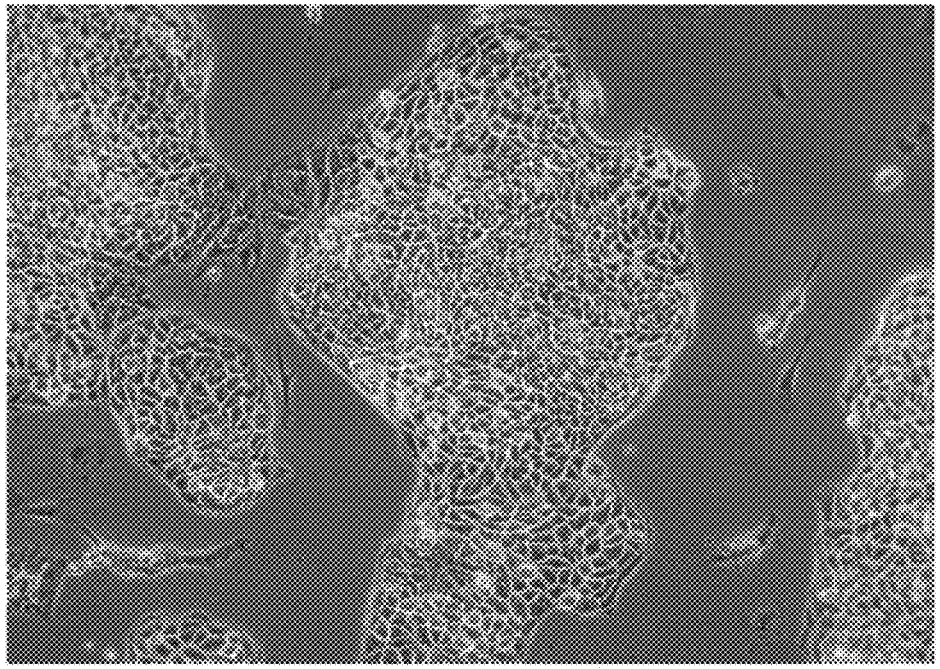

FIG. 3 shows light microscopy images at high confluency at 50× magnification (A) and low confluency at 200× magnification (B) of hPSC expanded for three passages in the stem cell culture medium containing activin a and trimipramine (as defined in Example 1). The homogeneous culture stably exhibits the prototypical morphological growth pattern of human pluripotent stem cells indicated a high nuclear:cytoplasmic ratio and smooth colony borders. Signs of differentiation are absent.

Figure 4:
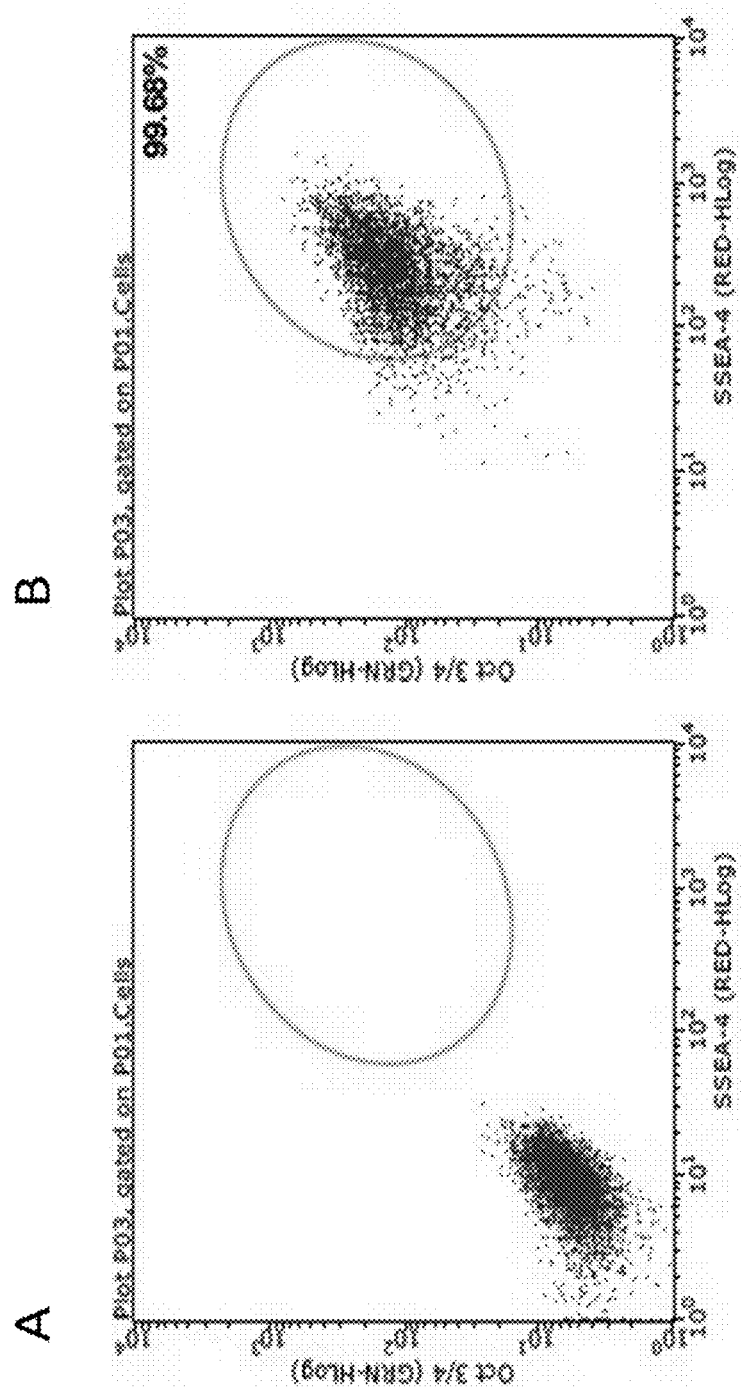

FIG. 4 shows the results of a flow cytometry analysis of hPSC pluripotency marker expression after three passages in the stem cell culture medium containing activin a and trimipramine (as defined in Example 1). The x-axis depicts SSEA-4 expression, the y-axis shows Oct-3/4 expression. A) negative control, B) double staining for Oct-3/4 and SSEA-4. More than 99% of the expanded hPSC are double positive for the pluripotency marker profile Oct-3/4/SSEA-4 after three consecutive passages in the established hPSC culture medium in the absence of exogenously added FGF-2.

Figure 5:
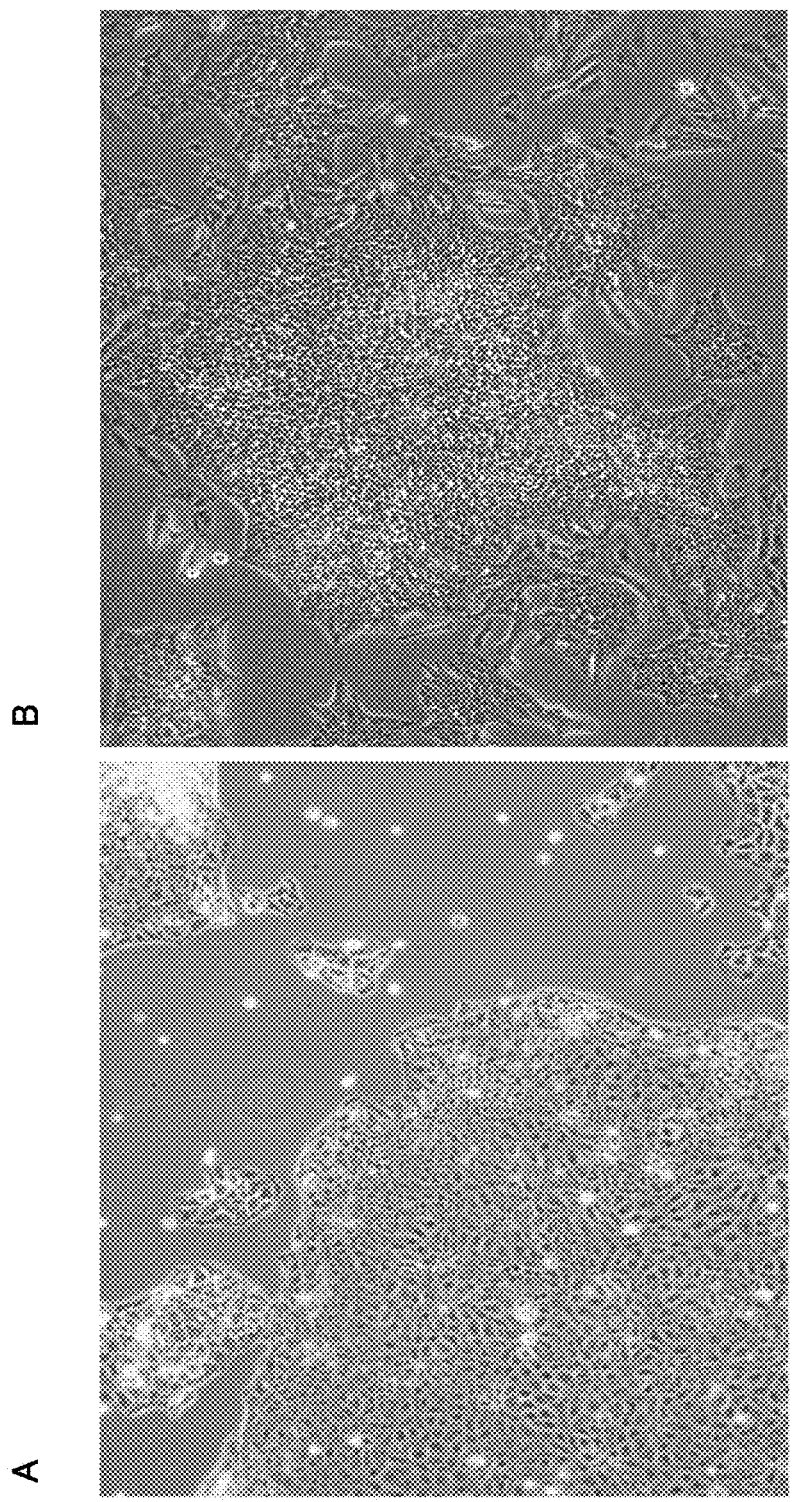

FIG. 5 shows light microscopy images at 100× magnification of the hPSC line WTSli026-A cultured for nine consecutive passages (A) in the stem cell culture medium containing trimipramine and activin a (as defined in Example 1) and for comparison (B) in a hPSC culture medium comprising FGF-2 and TGF-β1 (as defined in Example 9) for eight passages.

Figure 6:
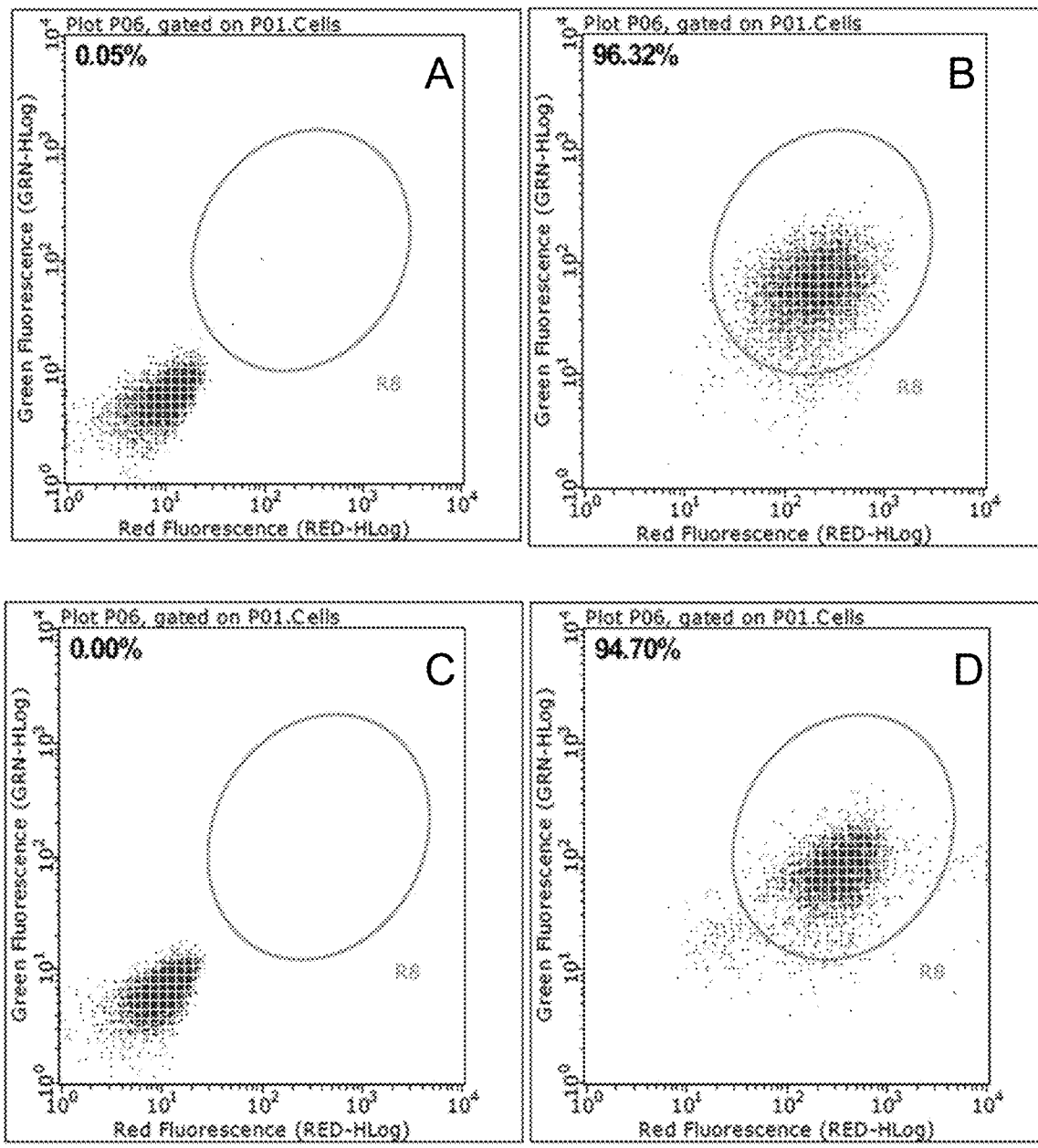

FIG. 6 shows the results of a flow cytometry analysis of hPSC pluripotency marker expression in the hPSC line WTSli026-A after nine passages (A+B) in the stem cell culture medium containing trimipramine and activin a (as defined in Example 1) and after eight passages (C+D) in a hPSC culture medium comprising FGF-2 and TGF-β1 (as defined in Example 9). The x-axis depicts SSEA-4 expression, the y-axis shows Oct-3/4 expression. A+C represent the negative control, B+D represent double staining for Oct-3/4 and SSEA-4.

DETAILED DESCRIPTION OF THE INVENTION

In order to provide a clear and consistent understanding of the specification and claims, and the scope to be given such terms, the following definitions are provided.

The term "ingredient" as used herein refers to any compound, whether of chemical or biological origin, that can be used in cell culture media to maintain or promote the growth or proliferation of cells. The terms "component" and "ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain growth of cells ex vivo can be selected by those of skill in the art, in accordance with the particular need.

The terms "medium", "cell culture medium," "culture medium" and "medium formulation" as used herein refer to a nutritive solution for culturing or growing cells.

"Cell culture" as used herein means cells or tissues that are maintained, cultured or grown in an artificial, in vitro environment. The terms "cultivating" and "culturing" are synonymous.

The terms "human pluripotent stem cell" or "hPSC" refer to undifferentiated biological cells of human origin that can differentiate into nearly all cells, excluding extra-embryonic tissues. hPSCs can be divided into human embryonic stem cells (ESC) and induced pluripotent stem cells (iPS). ESC are pluripotent stem cells derived from the inner cell mass of a blastocyst, an early-stage preimplantation embryo. Thus, the terms "human embryonic stem cell" or "hESC" refers to pluripotent stem cells derived from the human embryo. Induced pluripotent stem cells in contrast, can be generated from adult cells. Thus, the terms "induced pluripotent stem cell" or "iPSC" as used herein relates to a type of pluripotent stem cell that can be generated directly from adult cells. Accordingly, the term "human induced pluripotent stem cell" or "hiPSC" refers to iPCS generated directly from human adult cells.

The transformation of an undefined stem cell into a more specialized cell type is called "differentiation". Accordingly, the term "stem cell differentiation" as used herein describes the specialization of an undefined stem cell. The potential to differentiate into more specialized cell types is called potency. Thus the terms "potency" or "differentiation potential" specifies the potential of the stem cell to transform into a more specialized cell type. Stem cells can be classified according to their differentiation potential. Stem cells with the ability to differentiate into embryonic and extraembryonic cell types are called totipotent. Such cells can construct a complete, viable organism. The descendants of totipotent cells are pluripotent stem cells that can differentiate into nearly all cells, i.e. cells derived from any of the three germ layers. More specialized cells are called multipotent stem cells, which can differentiate into a number of cells, but only those of a closely related family of cells. Stem cells that can differentiate into only a few cells, such as lymphoid or myeloid stem cells, are oligopotent stem cells. Unipotent cells can produce only their own cell type but have the property of self-renewal, which distinguishes them from non-stem cells.

A "chemically defined medium" as used herein is a medium in which all ingredients and concentrations are known. It is in particular "serum-free", i.e. the medium contains no serum (e.g., fetal bovine serum (FBS), human serum, horse serum, goat serum, etc.).

The terms "serum-free culture conditions" and "serum-free conditions" refer to cell culture conditions that exclude serum of any type.

By "culture vessel" it is meant glass containers, plastic containers, or other containers of various sizes that can provide an aseptic environment for growing cells. For example, flasks, single or multiwell plates, single or multi-well dishes, or multiwell microplates can be used.

The terms "feeding" and "medium-change" as used herein refer to replacing the medium in which cells are cultured. The term "passage" and "passaging" as used herein means transferring some or all cells from a previous culture to fresh cell culture medium. For established hPSC cultures feeding intervals must be empirically determined for each hPSC line. The chemically defined culture medium according to the invention supports extended media change intervals of up to 72 hours. However, for culture initiation a daily media change is recommended during the first 2-3 days.

The term "salt" or "inorganic salt" as used herein refers to salt of elements that are present in the cell culture medium.

A "buffer component" as used herein is a substance used to maintain the acidity (pH) of a solution, i.e. the culture medium, near a chosen value. The function of a buffer component in tissue cultures is to maintain the pH in a narrow suitable range and to prevent deleterious pH-fluctuations which may occur by acidification of the culture medium by cellular metabolites, e.g. lactate.

A "physiological range" describes the presence of a substance in an organism or parts thereof in naturally occurring concentrations. Within these concentrations said substance is involved in biochemical processes in the organism or parts thereof.

Typically, the concentration of a substance in an organism or parts thereof is given as average concentration. Accordingly, the terms "lower physiological range" or a "higher physiological range" refer to concentrations of the substance which are below or above the average concentration of the substance, respectively.

The present invention is inter alia based on the finding that the combination of a compound of the group of Functional Inhibitors of Acid Sphingomyelinase (FIASMAs), namely trimipramine, and a TGF-β superfamily member, namely activin a, within a chemically defined cell culture medium supports the efficient in vitro expansion of undifferentiated pluripotent stem cells. In particular, the medium does not require exogenously added FGF-2.

The present invention provides a chemically defined medium for eukaryotic cell culture, comprising water, at least one carbon source, one or more vitamins, one or more salts, one or more fatty acids, one or more buffer components, selenium, at least one substance of the group of FIASMAs and at least one polypeptide of the TGF-β superfamily with the ability to inhibit stem cell differentiation.

As shown in the examples, the chemically defined medium according to the invention is a valuable tool for the expansion and/or maintenance of pluripotent stem cells. The specific combination of the FIASMA trimipramine and activin a, which is a member of the TGF-β superfamily, within the chemically defined medium according to the invention allows rapid expansion of hESC while maintaining typical properties of pluripotent stem cells. The cells have a typical growth pattern of smooth-edged colonies and still express pluripotency markers Oct-3/4 and SSEA-4 after several passages.

"Activin a" as used herein refers to the homodimer of the inhibin beta A subunit as defined by accession number P08476 of the UniProtKB database (www.uniprot.org/uniprot/) and functional equivalents thereof. Activin a is a member of the TGF-β superfamily. The TGF-β superfamily is a large group of structurally related cell regulatory proteins. Members of the TGF-β superfamily play important roles in e.g. proliferation, differentiation and other functions in many cell types. Typically, the proteins are homo- or heterodimers, but the dimer represents the active form of the protein which is built up of two chains being linked by a single disulfide bond.

In established stem cell media formulations TGF-β, the most prominent member of the TGF-β superfamily, has been used to support self-renewal of hPSC. In the absence of TGF-β, self-renewal—either alone or in combination with further active substances—can also be observed for cells cultured in a medium comprising other members of the TGF-β superfamily, namely nodal, myostatin, growth differentiation factor 3 (GDF3), or activins. However, the identified proteins do not activate the classical TGF-β activated downstream signaling pathway but trigger alternative ones e.g. the ErbB3—or Nodal/Activin-signaling pathway (Pera and Tam, 2010). This finding indicates the presence of distinct intracellular signaling pathways regulating stem cell differentiation.

In one embodiment of the invention the chemically defined medium according to the invention comprises a FIASMA and a polypeptide of the TGF-β superfamily with the ability to inhibit stem cell differentiation. According to a further embodiment the polypeptide of the TGF-β superfamily is not TGF-β.

Activin a, for example, binds to the ActRIIA receptor and initiates the rapid recruitment, phosphorylation, and activation of ActRI receptor. This then activates the SMAD2/3 cascade by phosphorylation and subsequent activation of cytoplasmic SMAD proteins. These proteins translocate to the nucleus and interact with SMAD4 resulting in gene expression of a large variety of genes including those responsible for regulating cell differentiation.

Thus, in one embodiment of the invention the at least one polypeptide of the TGF-β superfamily is selected from the group consisting of activins, nodal, myostatin and GDF3.

In a further embodiment of the invention, the member of the TGF-β superfamily is selected from the group of activins, as activins activate similar heteromeric serin/threonin-specific protein kinases responsible for regulation of stem cell differentiation. In a preferred embodiment, the member of the TGF-β superfamily is activin a.

The present examples indicate that the use of activin a alone results in rapid differentiation of hPSC. In addition to the cell lines tested herein, activin a was not able to extend pluripotency of other established hPSC, in particular hESC (Vallier et al., 2005).

FIASMAs share conserved physicochemical properties throughout all molecules within this class. All hitherto identified FIASMAs harbor a basic nitrogen atom and a lipophilic part, resulting in a cationic amphiphilic character of the molecule. Due to these structural and functional similarities, it is reasonably expected that other FIASMAs exhibit the same effect as it is shown for trimipramine in the examples.

Among the FIASMAs, there is a group of molecules with increased structural similarity to trimipramine e.g. mepacrine, promethazine and profenamine. Interestingly, this group of molecules, in particular trimipramine, mepacrine, promethazine, and profenamine, has been identified to induce the expression of known pluripotency markers SSEA-3, SSEA-4 TRA-1-60, TRA-1-81 and OCT4 in stem cells when cultured in the absence of FGF2 (Kumagai et al., 2013). This correlation allows the transfer of the results presented in the examples to other members of the FIASMA group, in particular, mepacrine, promethazine, and profenamine.

Accordingly, in another embodiment of the invention the FIASMA is selected from the group of trimipramine, mepacrine, promethazine and profenamine. In a preferred embodiment of the invention the FIASMA is trimipramine.

The examples reveal that trimipramine alone is not fully effective for the maintenance of undifferentiated proliferation of hPSC. In fact, the cells remain in an undifferentiated state while the proliferation of hPSC is inhibited. Consequently, the use of trimipramine alone only prolongs the pluripotency of undifferentiated stem cells.

As trimipramine and activin a alone are not sufficient to support proliferation and maintenance of undifferentiated pluripotent stem cells both substances may have a synergistic effect when employed in combination.

Indeed, the inventors have surprisingly found that the combination of trimipramine and activin a allows proliferation and maintenance of pluripotent stem cells. The combination of trimipramine and activin a in a chemically defined cell culture medium may trigger signaling pathways allowing for long-term cultivation of a broad range of pluripotent stem cells.

In a further embodiment according to the invention the FIASMA in the chemically defined medium is trimipramine and the polypeptide of the TGF-β superfamily is activin a.

According to one embodiment the FIASMA has a molecular weight in the range from 250 g/mol to 500 g/mol. Trimipramine is a relatively small molecule with a molecular weight of 294.4 g/mol. Profenamine has a molecular weight of 312.4 g/mol, Mepacrine has a molecular weight of 399.9 g/mol, and Promethazine has a molecular weight of 284.4 g/mol. Due to the relatively small molecular size the FIASMA can enter multi-layer tissues. Within the cell, the FIASMA may directly interact with important regulators of cell differentiation. Other active agents known to inhibit stem cell differentiation, such as growth factors, rely on receptor molecules for signal transduction into the cell. Signal transduction via receptors is typically activated when a certain threshold is reached, whereas the direct interaction of the FIASMAs with regulating proteins can occur in a concentration-dependent manner.

Growth factors traditionally used for activation of pluripotency and self-renewal signaling pathways, e.g. FGF-2 and TGF-β11, represent highly potent, yet very unstable, small proteins with a short biological half-life of only approx. 5-7 hours for FGF-2 and 50 minutes for TGF-β1 under cell culture conditions. As a result, the biological activity of the added growth factors diminishes quickly. In order to prevent differentiation of hPSC, traditional hPSC culture systems require a daily media change interval.

In addition, in order to lessen potential differentiation effects (due to the short half-life of the used growth factors) within the daily media change interval, supraphysiological concentrations of up to 100 ng/ml FGF-2 are used in some defined and feeder-free hPSC media, such as mTeSR or Essential 8. However, supraphysiological concentrations of FGF have been demonstrated to impair proliferation and self-renewal of hPSC (Furue et al., 2008). Indeed, research undertakes efforts to develop growth factor variants with improved thermal stability.

In contrast FIASMA, synthetic chemicals of organic nature, do not only act in a more direct mechanism as compared to receptor-mediated effects of traditional growth factors but also exhibit significant advantages with regard to their half life, allowing for considerably extended media change intervals. Trimipramine has a half-life of 23 hours, a threefold higher value in comparison to FGF-2. Concordantly, the chemically defined medium according to the invention supports media change intervals of up to 72 hours, even at high cell densities, with robust inhibition of hPSC differentiation—a significant technical benefit for routine hPSC culture.

Positive effects on maintaining stem cell pluripotency using the culture medium according to the invention can be already observed with a concentration of 0.1 mg/L of the FIASMA and remarkable results can be achieved when applied in a concentration of up to 10 mg/L. At concentrations higher than 15 mg/L, FIASMAs may develop cytotoxic effects.

Thus, in one embodiment according to the invention the concentration of the at least one FIASMA in the chemically defined medium is in the range of 0.1 mg/L to 10 mg/L.

Increasing efficiency in regard to maintaining pluripotency is observed with increasing concentration of the FIASMA from about 0.5 mg/L until a concentration of about 5 mg/L depending on which FIASMA is used. Thus, in another embodiment of the invention, the concentration of the FIASMA is in the range of 0.5 mg/L to 5 mg/L.

For trimipramine robust results were achieved when used in concentrations of 1 mg/L to 4 mg/L. Thus, in a further embodiment the concentration of the FIASMA within the chemically defined medium according to the invention is in the range of 1 mg/L to 4 mg/L. In particular the concentration of the FIASMA in the chemically defined medium according to the invention is 1 mg/L, 1.5 mg/L, 2 mg/L, 2.5 mg/L, 3 mg/L, 3.5 mg/L or 4 mg/L.

In one embodiment the chemically defined medium according to the invention comprise trimipramine in a concentration range from 1 mg/L to 4 mg/L, in particular the concentration is of is 1 mg/L, 1.5 mg/L, 2 mg/L, 2.5 mg/L, 3 mg/L, 3.5 mg/L or 4 mg/L. In another embodiment the chemically defined medium according to the invention comprise mepacrine in a concentration of is 1 mg/L, 1.5 mg/L, 2 mg/L, 2.5 mg/L, 3 mg/L, 3.5 mg/L or 4 mg/L. In yet another embodiment the chemically defined medium according to the invention comprise promethazine in a concentration of is 1 mg/L, 1.5 mg/L, 2 mg/L, 2.5 mg/L, 3 mg/L, 3.5 mg/L or 4 mg/L. In a further embodiment the chemically defined medium according to the invention comprise profenamine in a concentration of is 1 mg/L, 1.5 mg/L, 2 mg/L, 2.5 mg/L, 3 mg/L, 3.5 mg/L or 4 mg/L.

The inventors also found that depending on which member is used a relatively broad concentration range of the TGF-β superfamily member can be applied in the chemically defined medium according to the invention positively controlling the proliferation potential of the cultured cells. Already concentrations of the TGF-β superfamily member of 0.2 µg/L appear to have an effect. Without wanting to be bound to theory, it is assumed that concentrations of the TGF-β superfamily member above 200 µg/L may have harmful unspecific effects on the cells, partially via unconventional "non-canonical signaling". Thus, according to one embodiment the concentration of the at least one polypeptide of the TGF-β superfamily in the chemically defined medium according to the invention is in the range of 0.2 µg/L to 200 µg/L.

Moreover, concentrations ranging from 1 µg/L to 100 µg/L of TGF-β superfamily members sufficiently support proliferation and maintenance of undifferentiated pluripotent stem cells. Robust results were obtained with concentrations starting from 1 µg/L. However, concentrations above 100 µg/L exceed the physiological concentration of most of the TGF-β superfamily members. Thus, in a further embodiment the concentration of the at least one polypeptide of the TGF-β superfamily in the chemically defined medium according to the invention is in the range of 1 µg/L to 100 µg/L.

Cells cultured in the chemically defined medium according to the invention supplemented with 2 µg/L to 20 µg/L activin a robustly show that the majority of cells express typical pluripotency markers Oct3/4, Nanog, SSEA-4, and TRA-1-60 over several passages. GDF3 and/or myostatin in a concentration range of 1 µg/L to 50 µg/L trigger the expression of said pluripotency markers in vitro. In particular, GDF3 and/or myostatin in a concentration range of 10 µg/L to 20 µg/L showed a robust expression of said marker genes in in vitro cultured cells. For nodal, pluripotency marker expression could be observed when applied in concentrations ranging from 10 µg/L to 500 µg/L, in particular stably expression was achieved when nodal is present in the culture medium according to the invention in a concentration range of 50 µg/L to 200 µg/L.

In another embodiment, the concentration of the TGF-β superfamily member is in the range of 2 µg/L to 20 µg/L. In particular the concentration is 2 µg/L, 5 µg/L, 7.5 µg/L 10 µg/L, 12.5 µg/L, 15 µg/L or 20 µg/L.

In a preferred embodiment the chemically defined medium according to the invention comprises activin a in a concentration from 2 µg/L to 20 µg/L, in particular in a concentration of 2 µg/L, 5 µg/L, 7.5 µg/L 10 µg/L, 12.5 µg/L, 15 µg/L or 20 µg/L.

Without wanting to be bound to a theory, it may be beneficial to apply the FIASMA and the TGF-β superfamily member in a defined ratio in order to fine tune down stream cellular processes that are important for regulation of the differentiation of stem cells into mature cells.

Such regulating mechanism can involve the synchronization of activating and/or inhibiting signaling cascades important for regulation of the differentiation of cell to certain tissues. Typical signaling cascades that regulate differentiation of pluripotent stem cells are AKT-, SMAD-, Wnt/β/Catenin- and PI(3)K-signaling as well as the MEK/ERK cascade.

The FIASMA and the TGF-β superfamily member can be applied in a broad range of concentrations as outlined above. However, limits are present where the concentration is too low to activate necessary signaling pathways or where concentrations are too high the substances become cytotoxic or cells loose their pluripotency. In a concentration ratio of 50:1 (FIASMA:TGF-β superfamily member) the FIASMA is able to induce respective signaling pathways and the concentration of the TGF-β superfamily member allows the inhibition of differentiation without affecting the pluripotency. In a concentration ratio of 2000:1 the cells are viable, thus the FIASMA is not cytotoxic, and the concentration of the TGF-β superfamily member is sufficient to maintain pluripotency.

It has to be noted that the ratios are based on the concentration (WN) of the FIASMA and TGF-β superfamily member. Due to its lower molecular weight compared to the TGF-β superfamily member, the molar ratios within the chemically defined medium are even higher.

In one embodiment of the invention the at least one FIASMA and at least one polypeptide of the TGF-β superfamily are applied in a ratio between 2000:1 and 50:1 within the chemically defined medium according to the invention.

In another embodiment of the invention the chemically defined medium comprises trimipramine and activin a in a ratio between 2000:1 and 50:1.

As can be seen in the examples, proliferation and maintenance of undifferentiated pluripotent stem cells is achieved when cells are cultured in a chemically defined medium comprising trimipramine and activin a in concentrations resulting in a ratio of about 1000:1. The at least one FIASMA and at least one polypeptide of the TGF-β superfamily are applied in a ratio of 1000:1 in a further embodiment of the invention.

In another embodiment trimipramine and activin a are applied in a ratio of 1000:1 in the chemically defined medium according to the invention.

The present inventors also observed that changing the concentrations of the FIASMA and the TGF-β superfamily member resulting in a concentration ratio of 400:1 further stabilizes the cell culture in terms of proliferation and maintenance of pluripotency.

Thus, in a further embodiment the at least one FIASMA and at least one polypeptide of the TGF-β superfamily are applied in a ratio of 400:1 in the chemically defined medium according to the invention. In a preferred embodiment the ratio of trimipramine and activin a in the chemically defined medium is 400:1.

Moreover, the chemically defined medium according to the invention is universally applicable for different stem cell lines. Established cell lines exhibit variable medium requirements. The chemically defined medium covers a range of variable metabolic requirements of hPSC.

In order to provide a chemically defined medium, the use of serum is prevented. This leads to the need to replace serum within the media. Media with serum replacements are supplemented with purified proteins, peptones, or hydrolysates, mainly of animal or human origin. The use of human- or animal-derived substances in cell culture systems poses the potential risk of introduction contaminants or pathogens/viruses into the process and thus potentially into the final product. Thus, only a complete replacement of animal-derived substances by non-animal-derived products leads to a safe serum-free medium.

Thus, in one embodiment according to the invention the chemically defined medium is completely devoid of human- or animal-derived substances including proteins, amino acids, lipids, fatty acids and carbohydrates. Accordingly, in an embodiment the TGF-β superfamily member within the chemically defined medium of the invention is recombinant activin a.

The chemically defined medium of the invention provides an optimal culture environment for a well-controlled culture process, consistent and reproducible performance without applying growth factors like FGF-2 (bFGF) or TGF-β in unfavorably high concentrations. The use of growth factors in high concentrations evokes unwanted side effects as growth factors may trigger several other non-specific cellular responses besides growth and differentiation. Reducing unwanted side effects presents a challenge when culturing stem cells in growth factor supplemented media formulations, especially when extended media change intervals are required and/or preferred. The chemically defined medium according to the invention works with a more stable chemical replacement of the key growth factor FGF-2 for maintenance of pluripotency and self-renewal. The direct intracellular mode of action on relevant key signaling pathways as well as the improved thermal stability under cell culture conditions yield similar or even better results without the mentioned side effects. Furthermore the substitution of FGF-2 by a more stable chemical mimetic allows for the concomitant option for extended media change intervals as compared to classical growth factor-based hPSC media.

Thus, in one embodiment oft the invention, the chemically defined medium according to the invention is free of FGF-2 and/or TGF-β.

Albumin is a further important supplement of serum-free cell culture systems. Typically, albumin is introduced into the culture medium by so called serum-replacements. Natural albumin(s) derived from human (HSA) or bovine (BSA) but also recombinant albumin are typically used in cell culture. Many molecules found in vitro are unstable or destructive when they are not bound to a complex partner. A function of albumin is to bind, sequester and stabilize a range of important small molecules and ions. However, not all albumins have the same efficacy in cell culture. Thus, cell culture systems comprising albumin has to be tightly controlled.

To avoid these labor-intensive controlling of the cell culture system, the inventors have developed a media formulation that allows cell culture in a stable environment without albumin. According to a further embodiment the chemically defined medium according to the invention is free of albumin.

In another embodiment of the invention the chemically defined medium according to the invention is free of FGF-2, albumin and/or TGF-β1. In yet another embodiment of the invention the chemically defined medium according to the invention is free of FGF-2, albumin and TGF-β1.

In another embodiment the components of the chemically defined medium are each present in a concentration sufficient to support proliferation and/or maintenance of pluripotent stem cells, wherein the differentiation of the pluripotent stem cells is inhibited. The concentration of any ingredient is based on the total volume of the chemically defined medium.

The chemically defined medium according to the invention—like every medium for eukaryotic cell culture—contains water, at least one carbon source, one or more vitamins, one or more salts and selenium. These components are also referred to herein as "basic medium ingredients". In the preparation of the chemically defined medium according to the invention the basic medium ingredients may be provided by a basal medium. The term "basal medium" refers to any medium which supports growth of eukaryotic cells and which by supplement of additional ingredients can be used to form a medium for a cell culture according to the invention. The basal medium supplies salts, for example salts of magnesium, calcium, sodium and potassium and optionally salts of trace elements, as well as vitamins, a carbon source, a buffer system, and essential amino acids. Basal media which can be used in the present invention include but are not limited to Dulbecco's Modified Eagle's Medium (DMEM), Ham's F-12, DMEM:F12, Minimal Essential Medium (MEM), Basal Medium Eagle (BME), RPMI 1640, F-10, α Minimal Essential Medium (αMEM), Glasgow's Minimal Essential Medium (G-MEM), and Iscove's Modified Dulbecco's Medium as well as combinations thereof. Preferred basal media formulations are Dulbecco's Modified Eagle's Medium (DMEM), Ham's F-12, or DMEM:F12.

Accordingly, the chemically defined medium comprises at least one carbon source.

The carbon source is preferably a hexose sugar selected from the group of glucose, galactose, mannose and fructose. The sugar is in particular D-glucose. The concentration of the carbon source is in the range from $5.8 \times 10^2$ mg/L to $5.8 \times 10^3$ mg/L. Preferably, the concentration of the carbon source in the culture medium is $8.8 \times 10^2$ mg/L to $4.8 \times 10^3$ mg/L, more preferably in the range from $1.8 \times 10^3$ mg/L to $3.8 \times 10^3$ mg/L.

Also the chemically defined medium comprises one or more salts. The salts are preferably selected from the groups consisting of calcium chloride dihydrate, magnesium chloride hexahydrate, magnesium sulfate anhydrous, potassium chloride, sodium chloride, sodium phosphate dibasic anhydrous, sodium phosphate monobasic anhydrous.

The salts are preferably present in a concentration sufficient to support proliferation and/or maintenance of pluripotent stem cells, wherein the differentiation of the pluripotent stem cells is inhibited. The salts are for example contained in the medium in following concentrations: calcium chloride dihydrate in a range of 40 mg/L to 400 mg/L, magnesium chloride hexahydrate in a range of 9 mg/L to 98 mg/L, magnesium sulfate anhydrous in a range of 8 mg/L to 88 mg/L, potassium chloride in a range of 37.4 mg/L to 374 mg/L, sodium chloride in a range of $1.11 \times 10^3$ mg/L to $1.11 \times 10^4$ mg/L sodium phosphate dibasic anhydrous in a range of 7.8 mg/L to 78 mg/L, and sodium phosphate monobasic anhydrous in a range of 12.4 mg/L to 124 mg/L.

The correct adjustment of the osmolality of the culture medium is of high importance because it has been shown, that cell growth is affected when the osmolality is too low or too high. Typically, the osmolality of eukaryotic cell culture is within the range from 260 mOSM/kg to 360 mOSM/kg. Thus, in one embodiment the osmolality of the cell culture medium according to the invention is in the range from 260 mOSM/kg to 360 mOSM/kg, preferably in a range of 270 mOSM/kg to 290 mOSM/kg.

Further basic medium ingredients are the one or more vitamins. The one or more vitamins are preferably selected from D-biotin, D-Ca pantothenate, folic acid, nicotinamide, pyridoxal hydrochloride, pyridoxine hydrochloride, riboflavin, thiamine hydrochloride, vitamin B12, and ascorbic acid, including ascorbic acid-2-phosphate.

The vitamins are present in a concentration sufficient to support proliferation and/or maintenance of pluripotent stem cells, wherein the differentiation of the pluripotent stem cells is inhibited. The vitamins are for example contained in the medium in following concentrations: D-biotin in a range of $1.4 \times 10^{-3}$ mg/L to $1.4 \times 10^{-2}$ mg/L, D-Ca pantothenate in a range of 0.5 mg/L to 5 mg/L, folic acid in a range of 0.4 mg/L to 4 mg/L, nicotinamide in a range of 0.4 mg/L to 4 mg/L, pyridoxal hydrochloride in a range of 0.2 mg/L to 2 mg/L, pyridoxine hydrochloride in a range of $5.6 \times 10^{-3}$ mg/L to $5.6 \times 10^{-2}$ mg/L, riboflavin in a range of $7.8 \times 10^{-2}$ mg/L to $7.8 \times 10^{-1}$ mg/L, thiamine hydrochloride in a range of 0.8 mg/L to 8 mg/L, vitamin B12 in a range of 0.2 mg/L to 2 mg/L.

The chemically defined medium comprises one or more of the amino acids. The term "one or more amino acids" refers to native amino acids or their derivatives (e.g., amino acid analogs), as well as their D- and L-forms. The one or more of the amino acids are preferably selected from glycine, L-alanine, L-arginine, L-asparagine L-aspartic acid, L-cysteine, L-cystine, L-glutamic acid, L-histidine, L-isoleucine, L-leucine, L-lysine, L-methionine, L-phenylalanine, L-proline, L-serine, L-threonine, L-tryptophan, L-tyrosine, L-valine. More preferably, the chemically defined medium contains all of these amino acids.

The amino acids are preferably contained the medium in the concentration ranges defined below: Glycine in a range of 4.5 mg/L to 45 mg/L, L-alanine in a range of 1.7 mg/L to 17 mg/L, L-arginine hydrochloride in a range of 23 mg/L to 230 mg/L, L-asparagine monohydrate in a range of 2.5 mg/L to 25 mg/L, L-aspartic acid in the range of 1.7 mg/L to 17 mg/L, L-cysteine hydrochloride monohydrate in a range of 2.4 mg/L to 24 mg/L, L-cystine dihydrochloride in a range of 3.7 mg/L to 37 mg/L, L-glutamic acid in a range of 1.1 mg/L to 11 mg/L, L-histidine hydrochloride monohydrate in a range of 3.7 mg/L to 37 mg/L, L-isoleucine in a range of 17 mg/L to 170 mg/L, L-leucine in a range of 8.2 mg/L to 82 mg/L, L-lysine hydrochloride in a range of 16 mg/L to 160 mg/L, L-methionine in a range of 2 mg/L to 20 mg/L, L-phenylalanine in a range of 9.9 mg/L to 99 mg/L, L-proline in a range of 5.8 mg/L to 58 mg/L, L-serine in a range of 4.2 mg/L to 42 mg/L, L-threonine in a range of 7.4 mg/L to 74 mg/L, L-tryptophan in a range of 2.5 mg/L to 25 mg/L, L-tyrosine disodium salt dihydrate in a range of 14.5 mg/L to 145 mg/L, L-valine in a range of 9.5 mg/L to 95 mg/L.

According to one embodiment the chemically defined medium further comprises one or more dipeptides selected from the group consisting of L-alanyl-L-glutamine, glycyl-L-glutamine and N-acetyl-L-glutamine. Preferably the chemically defined medium according to the invention comprises L-alanyl-L-glutamine in a concentration range from 65 mg/L to 650 mg/L.

The trace element selenium is a basic component according to the invention. In an embodiment of the invention the selenium containing salt is present in a concentration in the range of 1 µg/L to 100 µg/L. In a further embodiment, selenium is present in a concentration in the range of 10 µg/L to 50 µg/L.

The chemically defined medium may additionally comprise a standard trace element selected from copper (Cu), iron (Fe), zinc (Zn). The chemically defined medium preferably comprises Fe. The chemically defined medium may for example comprise the standard trace elements Cu and Fe. Alternatively, the chemically defined medium may comprise Fe and Zn. More preferably, the chemically defined medium comprises Cu, Fe and Zn.

Cu, Fe and Zn are introduced into the chemically defined medium as a salt.

Preferably, Cu is introduced as cupric sulfate pentahydrate, Fe is introduced as ferric nitrate nonahydrate and/or ferrous sulfate heptahydrate, Zn is introduced as zinc sulfate heptahydrate.

Cu, Fe and Zn are preferably present in a concentration sufficient to support proliferation and/or maintenance of pluripotent stem cells, wherein the differentiation of the pluripotent stem cells is inhibited. For example the medium contains the following concentrations: cupric sulfate pentahydrate in a range of $2\times10^{-4}$ mg/L to $1.6\times10^{-3}$ mg/L, ferric nitrate nonahydrate in a range of $1.2\times10^{-2}$ mg/L to $1.2\times10-1$ mg/L, ferrous sulfate heptahydrate in a range of $7.5\times10^{-2}$ mg/L to $7.5\times10^{-1}$ mg/L, and zinc sulfate heptahydrate in a range of $4.7\times10^{-2}$ mg/L to $4.7\times10^{-1}$ mg/L.

The one or more fatty acids according to the invention may be selected from saturated and unsaturated fatty acids. The one or more fatty acids may example be selected from the group consisting of linoleic acid, arachidonic acid, linolenic acid, myristic acid, oleic acid, palmitic acid, stearic acid, myristoleic acid, palmitoleic acid, sapienic acid, elaidic acid, vaccenic acid, linoelaidic acid, eicosapentaenoic acid, erucic acid, caprylic acid, capric acid, lauric acid, arachidic acid, behenic acid, lignoceric acid, cerotic acid. Preferably, the fatty acid is linoleic acid.

In one embodiment according to the invention the chemically defined medium comprises one fatty acid, preferably in a concentration in the range of $4.6\times10^{-3}$ mg/L to $4.6\times10^{-2}$ mg/L.

The culturing of cells in a serum-free environment is a challenge because most cells rely on serum proteins to proliferate and maintain health. However, cells can be successfully moved out of serum by using substances that replace the key components of serum. Insulin and transferrin are two key components of serum and are commonly used to remove serum in culture. Insulin supports cell growth and regulates the cellular uptake and metabolism of glucose, amino acids, and lipids. Transferrin is an iron-binding glycoprotein. It facilitates extracellular iron storage, and transport. Transferrin is also an important antioxidant and prevents the formation of free radicals under physiological conditions.

According to one embodiment of the chemically defined medium further comprises insulin or insulin substituents and/or transferrin or transferrin substituents. Each of these components is preferably present in the chemically defined medium in a concentration sufficient to support proliferation and/or maintenance of pluripotent stem cells, wherein the differentiation of the pluripotent stem cells is inhibited.

In a further embodiment according to the invention the chemically defined medium comprises insulin and transferrin. In a preferred embodiment of the invention, the chemically defined medium comprises recombinant insulin and recombinant transferrin.

According to another embodiment of the invention the concentration of transferrin is in the range of 0.1 mg/L to 100 mg/L, preferably in the range of 1 mg/L to 50 mg/L, more preferably in the range of 5 mg/L to 25 mg/L and/or the concentration of insulin is in the range of 0.1 mg/L to 100 mg/L, preferably in the range of 1 mg/L to 10 mg/L. Further components of the chemically defined medium are preferably used in the following concentration ranges: Putrescine dihydrochloride is preferably present in the chemically defined medium in the range of $3\times10^{-2}$ mg/L to $3\times10^{-1}$ mg/L, sodium pyruvate is preferably present in the chemically defined medium in the range from 6.6 mg/L to 66.0 mg/L, thioctic acid is preferably present in the chemically defined medium in the range from $3\times10^{-2}$ mg/L to $3\times10^{-1}$ mg/L, thymidine is preferably present in the chemically defined medium in the range from $5\times10^{-2}$ mg/L to $5\times10^{-1}$ mg/L, hypoxanthine is preferably present in the chemically defined medium in the range from 0.33 mg/L to 3.3 mg/L, myo-inositol is preferably present in the chemically defined medium in the range from 4.2 mg/L to 42 mg/L, choline chloride is preferably present in the chemically defined medium in the range from 1 mg/L to 11 mg/L.

According to one embodiment the chemically defined medium comprises a buffer component selected from inorganic bicarbonate, inorganic phosphate or 4-(2-hydroxyethyl)-1-piperazineethanesulfonic acid (HEPES).

The chemically defined medium according to the invention preferably comprises additionally one or more radical scavengers. Examples of such radical scavengers are glutathione, tocopherol acetate, β-mercaptoethanol, dithiothreitol (DTT), N-acetyl-L-cysteine (NAC), the vitamin ascorbic acid, either L-ascorbic acid or its stable phosphate form.

According to one embodiment a further ingredient of the chemically defined medium is ascorbic acid, preferably in a concentration sufficient to support proliferation and/or maintenance of pluripotent stem cells, wherein the differentiation of the pluripotent stem cells is inhibited. Ascorbic acid is present in the chemically defined medium in a concentration in the range of 3 mg/L to 300 mg/L, preferably in the range of 10 mg/L to 100 mg/L. Ascorbic acid is an important cofactor for several redox reactions. For example, it acts as a reducing agent by donating electrons and preventing oxidation to keep iron and copper atoms in their reduced states. As a radical scavenger, ascorbic acid has the advantage of minimizing the formation of potentially cytotoxic peroxyl radicals.

A preferred embodiment of the invention is a chemically defined medium comprising the components listed below. calcium chloride dihydrate, magnesium chloride hexahydrate, magnesium sulfate anhydrous, cupric sulfate pentahydrate, ferric nitrate nonahydrate, ferrous sulfate heptahydrate, potassium chloride, sodium chloride, sodium phosphate dibasic anhydrous, sodium phosphate monobasic anhydrous, zinc sulfate heptahydrate, D-glucose anhydrous, glycine, L-alanine, L-alanyl-L-glutamine, L-arginine hydrochloride, L-asparagine monohydrate, L-aspartic acid, L-cysteine hydrochloride monohydrate, L-cystine dihydrochloride, L-glutamic acid, L-histidine hydrochloride monohydrate, L-isoleucine, L-leucine, L-lysine hydrochloride, L-methionine, L-phenylalanine, L-proline, L-serine, L-threonine, L-tryptophan, L-tyrosine, L-valine, choline chloride, D-biotin, D-Ca pantothenate, folic acid, myo-inositol, nicotinamide, pyridoxal hydrochloride, pyridoxine hydrochloride, riboflavin, thiamine hydrochloride, vitamin B12, hypoxanthine, linoleic acid, phenol red sodium salt, putrescine dihydrochloride, sodium pyruvate, thioctic acid, thymidine, ascorbic acid-2-phosphate, recombinant insulin, sodium selenite, trimipramine maleate salt, recombinant activin a, recombinant transferrin.

In one embodiment the components are present in the following concentration ranges: calcium chloride dehydrate 40 mg/L to 400 mg/L, magnesium chloride hexahydrate 9 mg/L to 98 mg/L, magnesium sulfate anhydrous 8 mg/L to 88 mg/L, cupric sulfate pentahydrate $2\times10^{-4}$ mg/L to $1.6\times10^{-3}$ mg/L, ferric nitrate nonahydrate $1.2\times10^{-2}$ mg/L to $1.2\times10^{-1}$ mg/L, ferrous sulfate heptahydrate $7.5\times10^{-2}$ mg/L to $7.5\times10^{-1}$ mg/L, potassium chloride 37.4 mg/L to 374 mg/L, sodium chloride $1.11\times10^{3}$ mg/L to $1.11\times10^{4}$ mg/L, sodium phosphate dibasic anhydrous 7.8 mg/L to 78 mg/L, sodium phosphate monobasic anhydrous 12.4 mg/L to 124 mg/L, zinc sulfate heptahydrate $4.7\times10^{-2}$ mg/L to $4.7\times10^{-1}$ mg/L, D-glucose anhydrous $1.8\times10^{3}$ mg/L to $3.8\times10^{3}$ mg/L, glycine 4.5 mg/L to 45 mg/L, L-alanine 1.7 mg/L to 17 mg/L, L-alanyl-L-glutamine 65 mg/L to 650 mg/L, L-arginine hydrochloride 23 mg/L to 230 mg/L, L-asparagine monohydrate 2.5 mg/L to 25 mg/L, L-aspartic acid 1.7 mg/L to 17 mg/L, L-cysteine hydrochloride monohydrate 2.4 mg/L to 24 mg/L, L-cystine dihydrochloride 3.7 mg/L to 37 mg/L, L-glutamic acid 1.1 mg/L to 11 mg/L, L-histidine hydrochloride monohydrate 3.7 mg/L to 37 mg/L, L-isoleucine 17 mg/L to 170 mg/L, L-leucine 8.2 mg/L to 82 mg/L, L-lysine hydrochloride 16 mg/L to 160 mg/L, L-methionine 2 mg/L to 20 mg/L, L-phenylalanine 9.9 mg/L to 99 mg/L, L-proline 5.8 mg/L to 58 mg/L, L-serine 4.2 mg/L to 42 mg/L, L-threonine 7.4 mg/L to 74 mg/L, L-tryptophan 2.5 mg/L to 25 mg/L, L-tyrosine 14.5 mg/L to 145 mg/L, L-valine 9.5 mg/L to 95 mg/L, choline chloride 1 mg/L to 11 mg/L, D-biotin $1.4\times10^{-3}$ mg/L to $1.4\times10^{-2}$ mg/L, D-Ca pantothenate 0.5 mg/L to 5 mg/L, folic acid 0.4 mg/L to 4 mg/L, myo-inositol 4.2 mg/L to 42 mg/L, nicotinamide 0.4 mg/L to 4 mg/L, pyridoxal hydrochloride 0.2 mg/L to 2 mg/L, pyridoxine hydrochloride $5.6\times10^{-3}$ mg/L to $5.6\times10^{-2}$ mg/L, riboflavin $7.8\times10^{-2}$ mg/L to $7.8\times10^{-1}$ mg/L, thiamine hydrochloride 0.8 mg/L to 8 mg/L, vitamin B12 0.2 mg/L to 2 mg/L, hypoxanthine 0.33 mg/L to 3.3 mg/L, linoleic acid $4.6\times10^{-3}$ mg/L to $4.6\times10^{-2}$ mg/L, phenol red sodium salt 0.16 mg/L to 1.6 mg/L, putrescine dihydrochloride $3\times10^{-2}$ mg/L to $3\times10^{-1}$ mg/L, sodium pyruvate 6.6 mg/L to 66.0 mg/L, thioctic acid $3\times10^{-2}$ mg/L to $3\times10^{-1}$ mg/L, thymidine $5\times10^{-2}$ mg/L to $5\times10^{-1}$ mg/L, ascorbic acid-2-phosphate 10 mg/L to 100 mg/L, recombinant insulin 1 mg/L to 10 mg/L, sodium selenite 10 µg/L to 50 µg/L, trimipramine maleate salt 1 mg/L to 4 mg/L, recombinant activin a 2 µg/L to 20 µg/L, recombinant transferrin 5 mg/L to 25 mg/L.

Preferably components are present in the following concentrations: calcium chloride dihydrate $2.01\times10^{2}$ mg/L, magnesium chloride hexahydrate $4.90\times10^{1}$ mg/L, magnesium sulfate anhydrous $4.40\times10^{1}$ mg/L, cupric sulfate pentahydrate $7.80\times10^{-4}$ mg/L, ferric nitrate nonahydrate $6.00\times10^{-2}$ mg/L, ferrous sulfate heptahydrate $3.75\times10^{-1}$ mg/L, potassium chloride $1.87\times10^{2}$ mg/L, sodium chloride $5.60\times10^{3}$ mg/L, sodium phosphate dibasic anhydrous $3.91\times10^{1}$ mg/L, sodium phosphate monobasic anhydrous $6.24\times10^{1}$ mg/L, zinc sulfate heptahydrate $2.38\times10^{-1}$ mg/L, D-glucose anhydrous $2.90\times10^{3}$ mg/L, glycine $2.25\times10^{1}$ mg/L, L-alanine 8.90 mg/L, L-alanyl-L-glutamine $3.25\times10^{2}$ mg/L, L-arginine hydrochloride $1.18\times10^{2}$ mg/L, L-asparagine monohydrate $1.28\times10^{1}$ mg/L, L-aspartic acid 8.65 mg/L, L-cysteine hydrochloride monohydrate $1.23\times10^{1}$ mg/L, L-cystine dihydrochloride $1.88\times10^{1}$ mg/L, L-glutamic acid 5.88 mg/L, L-histidine hydrochloride monohydrate $1.89\times10^{1}$ mg/L, L-isoleucine $8.72\times10^{1}$ mg/L, L-leucine $4.13\times10^{1}$ mg/L, L-lysine hydrochloride $8.21\times10^{1}$ mg/L, L-methionine $1.03\times10^{1}$ mg/L, L-phenylalanine $4.97\times10^{1}$ mg/L, L-proline $2.93\times10^{1}$ mg/L, L-serine $2.10\times10^{1}$ mg/L, L-threonine $3.74\times10^{1}$ mg/L, L-tryptophan $1.26\times10^{1}$ mg/L, L-tyrosine $7.25\times10^{1}$ mg/L, L-valine $4.76\times10^{1}$ mg/L, choline chloride 5.39 mg/L, D-biotin $6.83\times10^{-3}$ mg/L, D-Ca pantothenate 2.69 mg/L, folic acid 2.39 mg/L, myo-inositol $2.14\times10^{1}$ mg/L, nicotinamide 2.22 mg/L, pyridoxal hydrochloride 1.20 mg/L, pyridoxine hydrochloride $2.79\times10^{-2}$ mg/L, riboflavin $3.94\times10^{-1}$ mg/L, thiamine hydrochloride 4.12 mg/L, vitamin B12 1.09 mg/L, hypoxanthine 1.68 mg/L, linoleic acid $2.31\times10^{-2}$ mg/L, phenol red sodium salt $8.25\times10^{-1}$ mg/L, putrescine dihydrochloride $1.58\times10^{-1}$ mg/L, sodium pyruvate $3.30\times10^{1}$ mg/L, thioctic acid $1.58\times10^{-1}$ mg/L, thymidine $2.56\times10^{-1}$ mg/L, ascorbic acid-2-phosphate $2.75\times10^{1}$ mg/L, recombinant insulin 2.80 mg/L, sodium selenite $3.32\times10^{-2}$ mg/L, trimipramine maleate salt 2.00 mg/L, recombinant activin a $2.55\times10^{-3}$ mg/L, recombinant transferrin $1.76\times10^{1}$ mg/L.

The ingredients of the chemically defined medium can be combined by any method known in the art.

The chemically defined medium according to the invention may be prepared according to the following protocol. First, 90% of the final volume cell culture grade water is placed in a mixing vessel. The weighed amounts or appropriate quantities of stock solutions of the referring substance are subsequently added under permanent stirring. Finally, the volume is adjusted and the medium is filter-sterilized using a 0.22 µm filter unit.

The chemically defined medium according to the invention is suitable for eukaryotic cell culture. Thus, the present invention further provides the use of the chemically defined medium for culturing eukaryotic cells. As can be seen in the examples, the chemically defined medium according to the invention is in particular useful for culturing human pluripotent stem cells. Accordingly, in another embodiment the chemically defined medium of the invention can be used for culturing of human pluripotent stem cells preferably, human induced pluripotent stem cells.

According to an embodiment of the use of the chemically defined culture medium the cells are no embryonic stem cells and are not derived from embryonic stem cells. As shown in the examples, the chemically defined medium is in particular useful for the cultivation of hiPSC derived from human foreskin fibroblasts (SBI #SC101A-1) as well as for the two hiPS reference cell lines WTSli026-A and WTSli046-A.

Various types of stem cells are well characterized and techniques to reliably identify these cells have been developed. As an example, testing for pluripotency marker expression patterns, e.g. Oct-3/4, Nanog, SSEA and Tra antigens is also currently widely accepted as an indirect proof of a pluripotent state.

Thus, in one embodiment the inhibition of differentiation of the pluripotent stem cells indicated by the expression of pluripotency markers Oct-3/4, Nanog, Sox2, TRA-1-60, TRA-1-81, TRA-2-54 and/or SSEA-4.

Often, cells derived from vertebrates are anchorage-dependent—such as pluripotent stem cells—and have to be cultured on a suitable substrate that is specifically treated to allow for cell adhesion and support of self-renewal. However, many cell lines can also be adapted for suspension culture. In contrast to suspension culture, an adherent cell culture has several benefits. An adherent cell culture is appropriate for most cell types including stem cells. It also allows microscopic analysis for easy visual inspection. According to one embodiment the culturing of pluripotent stem cells is performed as an adherent cell culture.

For adherent cell culture, culture vessels are preferably coated with extracellular matrix proteins in order to provide a scaffold that cells can bind to using adhesive transmembrane molecules such as integrins. The terms "extracellular matrix", "ECM" or "basement membrane-like matrix" as used herein, describe composition of a variety of biologically active molecules that can be used to coat the culture vessel to provide such a scaffold. For use as extracellular matrices glycoproteins like laminins, vitronectin, fibrous proteins like collagen or elastin, synthetic peptides—so called ECM mimetics, E-cadherin, gelatin but also protein mixtures like Matrigel have been established.

As used herein, the term "xeno-free" describes the use of substances or ingredients that are not derived from another animal source than the cells used in the cell culture. Synthetically or recombinantly produced substances are also referred to as "xeno-free". For example, human laminin or vitronectin can be used as ECM in human cell culture, representing "xeno-free" ECMs.

According to a further embodiment the culturing of pluripotent stem cells is performed on an extracellular matrix. In a preferred embodiment the culturing of pluripotent stem cells is performed on a xeno-free extracellular matrix.

It is noted, that embodiments relating to a use of the chemically defined medium also apply to a method of culturing pluripotent stem cells in the chemically defined medium. Thus, the term "method" is synonymous for the term "use" and the one term can be replaced by the other.

The invention further relates to a cell culture system comprising pluripotent stem cells and the chemically defined medium according to the invention. According to one embodiment of the cell culture system, the pluripotent stem cells are human pluripotent stem cells, preferably human induced pluripotent stem cells (hiPSC). According to a further embodiment of the cell culture system the cells are no embryonic stem cells and are not derived from embryonic stem cells.

According to an embodiment, the cell culture system further comprises an extracellular matrix. In a preferred embodiment of the cell culture system, the extracellular matrix is xeno-free.

The invention further provides a kit for proliferation and/or maintenance of pluripotent stem cells in cell culture, comprising:
  a first composition comprising an extracellular matrix preparation, preferably a xeno-free extracellular matrix preparation,
  a second composition comprising water, at least one carbon source, one or more vitamins, one or more salts, one or more fatty acids and one or more buffer components, and
  a third composition comprising ascorbic acid, selenium, insulin, transferrin, activin a and trimipramine.

For the culture of pluripotent stem cells the first composition is used to prepare the culture vessel for adherent cell culture. The second and third composition are combined under sterile conditions and added to the prepared culture vessel. For culturing of pluripotent stem cells, the respective pluripotent stem cells are added to the prepared culture vessel. The cells are then cultured under suitable conditions depending on the pluripotent cell line used.

It has been demonstrated that in particular basal medium formulations are suitable for culturing human pluripotent stem cells. Thus, in one embodiment of the kit according to the invention the second composition comprises water, at least one carbon source, one or more vitamins, one or more salts, one or more fatty acids and one or more buffer components. In a preferred embodiment the second composition is a basal medium selected from Dulbecco's Modified Eagle's Medium (DMEM), Ham's F-12, or DMEM:F12.

Supplementing the basal media formulaion with trimipramine and activin a allows for proliferation and/or maintenance of pluripotent stem cells in cell culture. It has been shown that supplementing the basal medium with selenium and ascorbic acid, as well as insulin and/or transferrin supports the expansion of pluripotent stem cells in vitro.

Thus, in a further embodiment the third composition comprises ascorbic acid, selenium, insulin, transferrin, activin a and trimipramine.

According to one embodiment of the kit, the first composition comprises a xeno-free extracellular matrix preparation. In order to facilitate a gentle but efficient subculture of pluripotent stem cells, the cultured cells can be dissociated. Thus, in another embodiment, the kit optionally comprises a fourth composition for dissociation of cells.

The dissociation of cells can be achieved either enzymetically or nonenzymatically, both support clump as well as single cell passage of the cells. Established enzymatical compositions like Collagenase IV and Accutase™ can be used as well as compositions facilitating cell dissociation nonenzymatically such as PBS/EDTA solution, versene, EDTA/glycerol/sodium citrate.

In a further embodiment of the kit, optionally a nonenzymatic composition for dissociation of cells is used.

Thus, in one embodiment of the invention, the kit for proliferation and/or maintenance of pluripotent stem cells in cell culture comprises:
  a first composition comprising an extracellular matrix preparation, preferably a xeno-free extracellular matrix preparation,
  a second composition comprising water, at least one carbon source, one or more vitamins, one or more salts, one or more fatty acids and one or more buffer components,
  a third composition comprising ascorbic acid, selenium, insulin, transferrin, activin a and trimipramine, and
  optionally a fourth composition for dissociation of cells.

The invention is further defined by the following non-limiting examples.

EXAMPLES

Example 1—Preparation of a Chemically Defined Medium According to the Invention A stem cell culture medium, which is a chemically defined medium according to the invention, was prepared in the following way. First, a mixing vessel is filled up to 90% of the final volume with cell culture grade water. The weighed amounts or appropriate quantities of stock solutions of components are subsequently added under permanent stirring. Osmolality is adjusted to 280 mOSM/kg using NaClsolution. After solving all components the volume is adjusted and the medium is filter-sterilized. The final medium had the following composition: calcium chloride dihydrate $2.01 \times 10^2$ mg/L, magnesium chloride hexahydrate $4.90 \times 10^1$ mg/L, magnesium sulfate anhydrous $4.40 \times 10^1$ mg/L, cupric sulfate pentahydrate $7.80 \times 10^{-4}$ mg/L, ferric nitrate nonahydrate $6.00 \times 10^{-2}$ mg/L, ferrous sulfate heptahydrate $3.75 \times 10^{-1}$ mg/L, potassium chloride $1.87 \times 10^2$ mg/L, sodium chloride $5.60 \times 10^3$ mg/L, sodium phosphate dibasic anhydrous $3.91 \times 10^1$ mg/L, sodium phosphate monobasic anhydrous $6.24 \times 10^1$ mg/L, zinc sulfate heptahydrate $2.38 \times 10^{-1}$ mg/L, D-glucose anhydrous $2.90 \times 10^3$ mg/L, glycine $2.25 \times 10^1$ mg/L, L-alanine 8.90 mg/L, L-alanyl-L-glutamine $3.25 \times 10^2$ mg/L, L-arginine hydrochloride $1.18 \times 10^2$ mg/L, L-asparagine monohydrate $1.28 \times 10^1$ mg/L, L-aspartic acid 8.65 mg/L, L-cysteine hydrochloride monohydrate $1.23 \times 10^1$ mg/L, L-cystine dihydrochloride $1.88 \times 10^1$ mg/L, L-glutamic acid 5.88 mg/L, L-histidine hydrochloride monohydrate $1.89 \times 10^1$ mg/L, L-isoleucine $8.72 \times 10^1$ mg/L, L-leucine $4.13 \times 10^1$ mg/L, L-lysine hydrochloride $8.21 \times 10^1$ mg/L, L-methionine $1.03 \times 10^1$ mg/L, L-phenylalanine $4.97 \times 10^1$ mg/L, L-proline $2.93 \times 10^1$ mg/L, L-serine $2.10 \times 10^1$ mg/L, L-threonine $3.74 \times 10^1$ mg/L, L-tryptophan $1.26 \times 10^1$ mg/L, L-tyrosine $7.25 \times 10^1$ mg/L, L-valine $4.76 \times 10^1$ mg/L, choline chloride 5.39 mg/L, D-biotin $6.83 \times 10^{-3}$ mg/L, D-Ca pantothenate 2.69 mg/L, folic acid 2.39 mg/L, myo-inositol $2.14 \times 10^1$ mg/L, nicotinamide 2.22 mg/L, pyridoxal hydrochloride 1.20 mg/L, pyridoxine hydrochloride $2.79 \times 10^{-2}$ mg/L, riboflavin $3.94 \times 10^{-1}$ mg/L, thiamine hydrochloride 4.12 mg/L, vitamin B12 1.09 mg/L, hypoxanthine 1.68 mg/L, linoleic acid $2.31 \times 10^{-2}$ mg/L, phenol red sodium salt $8.25 \times 10^{-1}$ mg/L, putrescine dihydrochloride $1.58 \times 10^{-1}$ mg/L, sodium pyruvate $3.30 \times 10^1$ mg/L, thioctic acid $1.58 \times 10^{-1}$ mg/L, thymidine $2.56 \times 10^{-1}$ mg/L, ascorbic acid-2-phosphate $2.75 \times 10^1$ mg/L, recombinant insulin 2.80 mg/L, sodium selenite $3.32 \times 10^{-2}$ mg/L, trimipramine maleate salt 2.00 mg/L, recombinant activin a $2.55 \times 10^{-3}$ mg/L, recombinant transferrin $1.76 \times 10^1$ mg/L.

Example 2—Initiation of hPSC Cultures 2.1 Extra Cellular Matrix (ECM) Coating of the Culture Vessel The culture vessel was coated with 0.5 μg/cm² of recombinant human vitronectin as ECM. For this, 100 μl of a diluted vitronectin solution per cm² of culture vessel surface is applied to the culture vessel with. The coated culture vessel is left for 2 hours at room temperature. The vitronectin solution was aspirated just before seeding the cells.

2.2 Plate the Cells (Day 0)

The cell line used in this experiment is the human foreskin fibroblast derived hiPS cell line SBI #SC101A-1 (obtainable from System Biosciences (SBI), Palo Alto, under the defined reference number).

The stem cell culture medium was prepared as described in Example 1. For cryopreserved cells, a ROCK-Inhibitor (10 μM Y-27632 or 2 μM Thiazovivin) is added to the stem cell culture medium. Alternatively, for existing proliferating cultures a clump passage was performed as described in Example 3 below.

The hPSCs were seeded in a 1:2 to 1:3 ratio (relative to the volume of the tissue culture vessel) into the ECM coated tissue culture vessel using an appropriate amount of culture medium. For example, 2-3 ml per well are used for 6-well plates and 15-25 ml for T-75 flasks.

2.3 Let the Cells Attach (Day 0)

After plating, the subcultured hPSCs were allowed to attach overnight (12-24 hours).

2.4 Medium Change (Day 1)

A medium change was performed: the stem cell culture medium including non-attached cells was aspirated, washed once with Dulbecco's PBS, w/o $Ca^{2+}/Mg^{2+}$ and the cells were provided with fresh culture medium (w/o ROCK-Inhibitors).

2.5 Cell Expansion (Day 1+)

A media change was performed every 1-3 days. The hPSCs expanded until the single colonies touched each other (usually after 3-7 days) or colonies showed the first signs of differentiation evoked from their large size.

Example 3—Serial Passage of hPSC Cultures

The stem cell culture medium was aspirated and the hPSCs were washed twice with Dulbecco's PBS, w/o $Ca^{2+}/Mg^{2+}$. Next, 200-300 μl/cm² of dissociation buffer was added and the solution was incubated for 6-10 minutes in the incubator at 37° C. and 5% $CO_2$. The dissociation buffer was carefully aspirated and 1-5 ml of fresh culture medium was added. The colonies were flushed away from the surface using a serological pipet. In order to maintain cell clumps of sufficient size flushing of more than 4-5 times was avoided. Then, cell clumps were dispensed into new ECM-coated culture vessels with fresh stem cell culture medium and the culture was continued according to the cell attachment step (step 2.3) of Example 2.

Example 4—Culturing hPSCs in the Presence of Activin a

Induced pluripotent stem cells were cultured in the presence of the stem cell culture medium according to Example 1 without trimipramine in order to reproduce published observations that activin a on its own cannot fully support undifferentiated maintenance of most hPSC lines (Vallier et al., 2005; Xiao et al., 2006). Initiation of the hPSC culture was performed according to Example 2, followed by subculturing the cells according to Example 3.

While the culture exhibited significant cell proliferation, microscopic analysis revealed typical morphological changes indicative for differentiation even before the first passage. The initially homogeneous morphological pattern of the culture switched to an emphasized heterogeneous appearance: a high amount of elongated/enlarged cells (reflected in a reduced nuclear:cytoplasmic ratio in FIG. 1) as well as numerous floating detached cells are present. In hPSC these morphological attributes depict widely recognized, explicit signs of stem cell differentiation and loss of pluripotency.

As a result, activin a is not able to robustly support the maintenance of the tested hPSC line in an undifferentiated state under defined and feeder-free culture conditions.

Example 5—Culturing hPSCs in the Presence of Trimipramine

It was also aimed to reproduce the published partial self-renewal support capabilities of trimipramine in human pluripotent stem cells (Kumagai et al., 2013). For this purpose, hPSCs were cultured in the stem cell culture medium prepared according to Example 1 lacking activin a. Initiation of the hPSC culture was performed according to Example 2, followed by subculturing the cells according to Example 3.

Microscopic images showed, that in contrast to activin a, trimipramine alone is able to maintain the prototypical pluripotent morphological phenotype represented by roundish colonies with smooth-edged borders composed of cells with a high nuclear:cytoplasmic ratio. However, trimipramine is not sufficient to effectively expand the human pluripotent stem cells. As can be seen in FIG. 2, the initially plated cell clumps remain virtually the same size over 5 days of culture indicative for essential absence of cell proliferation.

Thus, pluripotent stem cells in a stem cell culture medium with trimipramine alone maintain their pluripotency but do not proliferate under chemically defined culturing conditions.

Example 6—Culturing hPSCs in the Presence of a Combination of Activin a and Trimipramine Each component on its own—activin a or trimipramine—does not allow for proper expansion and maintenance of undifferentiated hPSC in vitro but instead leads to a rapid loss of pluripotency or proliferation failure of the cultured cells, respectively. Even in the primary cultures of hPSC the described effects are obvious within 2 days after switching to the medium with the respective compound.

However, since activin a and trimipramine seem to independently and positively act on/mimic two different key signaling pathways for the maintenance of pluripotency, it is speculated that the combination of these two compounds might synergistically convey full self-renewal and expansion support for hPSC by simultaneous engagement of both types of signals.

To test this, pluripotent stem cells were cultured within a culturing system comprising the stem cell culture medium according to the Example 1, including activin a and trimipramine. Initiation of the hPSC culture was performed according to Example 2, followed by subculturing the cells according to Example 3.

6.1 Morphological Growth Pattern

Microscopic analysis showed, that supplementation of the stem cell culture medium with a combination of activin a and trimipramine allows for rapid expansion of the tested hPSC line with a constant passage interval of 3-4 days. As can be seen in FIG. 3, the culture exhibits a high nuclear:cytoplasmic ratio on a single cell level as well as the typical growth pattern of smooth-edged colonies. Floating differentiated cells are virtually absent between media changes.

6.2 Expression of Pluripotency Markers

In order to confirm the proper maintenance of the undifferentiated state on a molecular level, staining for the human pluripotency markers Oct-3/4 and SSEA-4 was performed after three passages in the stem cell culture medium containing activin a and trimipramine.

To do so, 1 h before starting the staining procedure, a media change was performed on an 80-90% confluent hPSC culture grown in a T25 TC-flask according to Example 2 and 3 in the stem cell culture medium prepared according to Example 1. 5 ml of human AB-serum (off the clot) are diluted with 45 ml of Dulbeccos PBS w/o $Ca^{2+}/Mg^{2+}$ (referred to as "PBS" in the following) and filtered through a 0.22 micron syringe filter with PES-membrane. The stem cell culture medium was aspirated from the cells and discarded. Then, the cells were washed twice with 5 ml PBS/0.5% BSA/2 mM EDTA. 5 ml hPSC dissociation buffer were added to the cells and incubated for 8 min at 37° C. and 5% $CO_2$ in the incubator. Microscopical evaluation showed shining borders of the attached colonies indicative for the beginning of the cell detachment process. The dissociation buffer was immediately aspirated and the loosely adherent hPSC colonies are washed away from the surface with 10 ml PBS by 3-5 recurrent flushes. Then, the cell clumps were completely dissociated by pipetting the cell suspension up and down for 5-10 times using a 10 ml serological pipet. Cells are counted using the Viacount Assay Reagent with a Muse Cell Analyzer (Millipore). The cell suspension was pelleted by centrifugation for 5 min at 200×g. The cells were resuspended at 100.000 cells/ml in human AB-serum (10% in PBS) and incubated at room temperature for 10 min. 3 ml of the cell suspension were pelleted by centrifugation for 5 min at 200×g. The supernatant was aspirated and the cells were resuspended in 300 µl of human AB-serum (10% in PBS). 100 µl of the cell suspension was transferred in each of two 15 ml conical tubes (sample 1 and sample 2).

To sample 2, 10 µl of PerCP-conjugated SSEA-4 antibody (R&D Systems No. FAB1435C) were added and incubated for 30 min at 4° C. in the dark. The untreated negative control sample 1 was co-incubated with sample 2. 2 ml of PBS with 0.5% BSA and 2 mM EDTA were added to each of sample 1 and sample 2 and pelleted by centrifugation for 5 min at 200×g. The cell pellets of sample 1 and sample 2 were each resuspended in 1 ml Fixing Buffer Reagent (Fix/Perm Cell Permeabilization Kit, Thermo Fisher No. GAS004) and incubated for 20 min at 4° C. in the dark. 2 ml of Washing Buffer Reagent (Fix/Perm Cell Permeabilization Kit, Thermo Fisher No. GAS004) was added to sample 1 and sample 2 and the cells were pelleted by centrifugation for 5 min at 200×g. The washing step was then repeated once more with 2 ml of Washing Buffer Reagent. The cell pellet of sample 2 was resuspended in 90 µl Washing Buffer Reagent and 10 µl of FITC-labeled Oct-3/4 antibody (R&D Systems No. IC-1759F) was added. The cell pellet of sample 1 was resuspended in 100 µl of Washing Buffer Reagent. Both samples were incubated at room temperature for 60 minutes in the dark. 2 ml of Washing Buffer Reagent was added to each of sample 1 and sample 2 and the cells were pelleted by centrifugation for 5 min at 200×g. The washing step was then repeated once more with 2 ml of Washing Buffer Reagent. The cell pellets each of sample 1 and sample 2 are resuspended in 0.5 ml PBS with 0.5% BSA and 2 mM EDTA and immediately analyzed using a Guava Flow Cytometer (Millipore) equipped with a blue laser.

FIG. 4 shows that more than 99% of the cells are stained double-positive for both markers strongly substantiating the prior morphological/expansion findings indicative for maintenance of stem cell properties.

It can be concluded, that the combination of trimipramine and activin a in the stem cell culture medium according to the invention is sufficient to sustain the undifferentiated expansion of hPSC as demonstrated by prolongation of self-renewal, a typical morphological growth pattern and pluripotency marker profile expression of the culture over multiple passages.

Example 7—Culturing of Further Induced Pluripotent Stem Cells

To confirm the applicability of the stem cell culture medium according to the invention for a broad spectrum of pluripotent stem cell lines, the experiments of Examples 4, 5 and 6 were repeated with further stem cell lines which are listed in Table 1. The growth experiments of these cell lines showed comparable results to SBI #SC101A-1.

TABLE 1

Further hPSC lines cultured in the stem cell
culture medium according to the invention.

| hPSC line | Description |
|---|---|
| WTSIi026-A (accession number at the European Bank for induced pluripotent Stem Cells (EBiSC)) | HipSci reference panel hiPSC line derived from human dermal fibroblast |
| WTSIi046-A (accession number at the EBiSC) | HipSci reference panel hiPSC line derived from human dermal fibroblast |

Example 8—all Established Types of ECM Appropriate for hPSC Culture can be Used To test the compatibility of further established types of ECMs with the stem cell culture medium according to the invention in cell culture, experiments were carried out using basement membrane-like matrices routinely used for hPSC culture. Tested ECMs are Matrigel™, Laminin-based matrices, vitronectin, cadherin-based matrices, and established ECM mimetic peptide matrices.

Each of the tested ECMs is used in cell cultures comprising the stem cell culture medium including activin a and trimipramine (as defined in Example 1). As controls, media formulations without activin a and without trimipramine are tested.

Cells cultured in the stem cell culture medium containing activin a and trimipramine exhibit a typical morphological growth pattern and pluripotency marker profile expression of the hPSCs over several passages similar to the results presented in experiment 6 irrespective on which ECM is used.

Thus, the stem cell culture medium according to the invention can be used in combination of virtually all established ECMs appropriate for hPSC culture and is not limited to the use in combination with a xeno-free ECM.

Example 9—Comparison of hPSCs Cultured in the Stem Cell Culture Medium Containing Activin a and Trimipramine and in a hPSC Culture Medium Comprising FGF-2 and TGF-β1

The combination of trimipramine and activin a in the stem cell culture medium according to the invention is sufficient to sustain the undifferentiated expansion of hPSC as demonstrated in Example 6.

To compare the applicability of the stem cell culture medium according to the invention and hPSC media comprising FGF-2 and TGF-β1 regarding the expansion of hPSC, hPSC were expanded within a culturing system comprising the stem cell culture medium containing activin a and trimipramine (as defined in Example 1) and a hPSC culture medium comprising FGF-2 and TGF-β11, respectively. The hPSC culture medium comprising FGF-2 and TGF-β1 was prepared according to Example 1 but with 10 ng/ml FGF-2 and 1 ng/ml TGF-β1 instead of trimipramine and activin a. Initiation of the hPSC culture was performed according to Example 2, followed by subculturing the cells according to Example 3.

9.1 Morphological Growth Pattern

Microscopic analysis of the hPSC cultured in the media above confirms that both media allow for rapid expansion of the tested hPSC line over eigth and nine passages, respectively (see FIG. 5). As can be seen in FIG. 5, the two cultures stably exhibit the prototypical morphological growth pattern of human pluripotent stem cells indicated by a high nuclear:cytoplasmic ratio and smooth colony borders. Floating differentiated cells are virtually absent between media changes.

The cells cultured in the stem cell culture medium containing trimipramine and activin a appear slightly larger, especially in areas of lower cell density, due to more pronounced spreading as compared to cells cultured in the hPSC culture medium comprising FGF-2 and TGF-β1. This observation is supported by longer incubation times with the dissociation buffer necessary to release the cells from the culture surface when cultured in the stem cell culture medium containing trimipramine and activin a. However, the observed cell size effect diminishes with increasing cell density.

9.2 Expression of Pluripotency Markers

In order to compare the maintenance of the undifferentiated state of hPSCs cultured in the stem cell culture medium containing trimipramin and activin a (as defined in Example 1) and hPSC cultured in the hPSC culture medium comprising FGF-2 and TGF-β1 on a molecular level, staining for the human pluripotency markers Oct-3/4 and SSEA-4 was performed as described in Example 6.2 after eight and nine passages, respectively.

More than 96% of the expanded hPSC are double positive for the pluripotency marker profile Oct-3/4 and SSEA-4 after nine consecutive passages in the stem cell culture medium containing trimipramine and activin a (see FIG. 6). As can be seen in FIG. 6, a comparable result is achieved after eight consecutive passages of the same cell line in the hPSC culture medium comprising FGF-2 and TGF-β1.

It can be concluded, that the combination of trimipramine and activin a in the stem cell culture medium according to the invention is sufficient to sustain the undifferentiated expansion of hPSC as demonstrated by prolongation of self-renewal, a typical morphological growth pattern and pluripotency marker profile expression of the culture over multiple passages comparable to hPSC culture media comprising FGF-2 and TGF-β1.

Many modifications and other embodiments of the invention set forth herein will come to mind to the one skilled in the art to which the invention pertains having the benefit of the teachings presented in the foregoing description and the associated figures.

Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

REFERENCES

1. Sanges, D. and M. P. Cosma, *Reprogramming cell fate to pluripotency: the decision-making signalling pathways.* Int J Dev Biol, 2010. 54(11-12): p. 1575-87.
2. Scholer, H. R., *The Potential of Stem Cells: An Inventory.* Humanbiotechnology as Social Challenge. Ashgate Publishing 2007. p. 28. ISBN 978-0-7546-5755-2.
3. Pauklin S, Pedersen R A, Vallier L., *Mouse pluripotent stem cells at a glance.* J Cell Sci, 2011, 124(22):3727-32.
4. Thomson J A, Itskovitz-Eldor J, Shapiro S S, Waknitz M A, Swiergiel J J, Marshall V S, Jones J M., *Embryonic stem cell lines derived from human blastocysts. Science*, 1998, 282(5391):1145-7.

5. Puri M C, Nagy A., *Concise review: Embryonic stem cells versus induced pluripotent stem cells: the game is on.* Stem Cells, 2012, (1):10-4.
6. Wilmut I, Schnieke A E, McWhir J, Kind A J, Campbell K H., *Viable offspring derived from fetal and adult mammalian cells.* Nature, 1997, 385(6619):810-3.
7. Bilic J, Izpisua Belmonte J C., *Concise review: Induced pluripotent stem cells versus embryonic stem cells: close enough or yet too far apart?* Stem Cells, 2012, (1):33-41.
8. Wenxiu Zhao, Xiang Ji, Fangfang Zhang, Liang Li, Lan Ma., *Embryonic Stem Cell Markers.* Molecules, 2012, (17):6196-6236.
9. Wobus A M, Boheler K R., *Embryonic stem cells: prospects for developmental biology and cell therapy.* Physiol Rev, 2005, 85(2):635-78.
10. Takahashi K, Tanabe K, Ohnuki M, Narita M, Ichisaka T, Tomoda K, Yamanaka S., *Induction of pluripotent stem cells from adult human fibroblasts by defined factors.* Cell, 2007, 131(5):861-72.
11. Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A., *Induced pluripotent stem cell lines derived from human somatic cells.* Science, 2007, 318(5858):1917-20.
12. González F, Boué S, Izpisua Belmonte J C., *Methods for making induced pluripotent stem cells: reprogramming à la carte.* Nat Rev Genet, 2011, 12(4):231-42.
13. Takahashi K, Yamanaka S., *Induction of pluripotent stem cells from mouse embryonic and adult fibroblast cultures by defined factors.* Cell, 2006, 126(4):663-76.
14. Sheridan S D, Surampudi V, Rao R R., *Analysis of embryoid bodies derived from human induced pluripotent stem cells as a means to assess pluripotency.* Stem Cells Int., 2012, 2012:738910.
15. Jaenisch R, Young R., *Stem cells, the molecular circuitry of pluripotency and nuclear reprogramming.* Cell, 2008, 132(4):567-82.
16. Ludwig, T. E., et al., *Derivation of human embryonic stem cells in defined conditions.* Nat Biotechnol, 2006, 24(2): 185-187.
17. U.S. Pat. No. 8,211,699 B2 (VIACYTE, INC.) 3 Jul. 2012 (03.07.2012)
18. Vallier, L., et al., *Activin/Nodal and FGF pathways cooperate to maintain pluripotency of human embryonic stem cells.* J Cell Sci, 2005, 118(Pt 19): 4495-4509.
19. Xiao, L., et al., *Activin A maintains self-renewal and regulates fibroblast growth factor, Wnt, and bone morphogenic protein pathways in human embryonic stem cells.* Stem Cells, 2006, 24(6): 1476-1486.
20. Vallier, L., et al., *Signaling pathways controlling pluripotency and early cell fate decisions of human induced pluripotent stem cells.* Stem Cells, 2009, 27(11): 2655-2666.
21. Zhang, Y., et al., *Small molecules, big roles—the chemical manipulation of stem cell fate and somatic cell reprogramming.* J Cell Sci, 2012, 125(Pt 23): 5609-5620.
22. Kumagai, H., et al., *Identification of small molecules that promote human embryonic stem cell self-renewal.* Biochem Biophys Res Commun, 2013, 434(4): 710-716.
23. Furue M K, Na J, Jackson J P, et al. *Heparin promotes the growth of human embryonic stem cells in a defined serum-free medium.* Proceedings of the National Academy of Sciences of the United States of America, 2008; 105(36):13409-13414.
24. Pera M F and Tam P P L. *Extrinsic regulation of pluripotent stem cells.* Nature, 2010, 465, 713-720.

The invention claimed is:

1. A chemically defined medium for eukaryotic cell culture, comprising water, at least one carbon source, one or more vitamins, one or more salts, one or more fatty acids, one or more buffer components, selenium, at least one substance of the group of Functional Inhibitors of Acid Sphingomyelinase (FIASMAs) and at least one polypeptide of the TGF-β superfamily with the ability to inhibit stem cell differentiation,
   wherein the chemically defined medium is free of FGF-2,
   wherein the chemically defined medium is completely devoid of human- or animal-derived substances,
   wherein the ratio between said FIASMA and said at least one polypeptide of the TGF-β superfamily is from 400:1 to 2000:1,
   wherein the concentration of the at least one FIASMA is in the range of 0.1 mg/L to 10 mg/L, and
   wherein the concentration of the at least one polypeptide of the TGF-β superfamily is in the range of 0.2 μg/L to 20 μg/L.

2. The chemically defined medium according to claim 1, wherein the FIASMA is selected from the group consisting of Trimipramine, Mepacrine, Promethazine and Profenamine.

3. The chemically defined medium according to claim 1, wherein the at least one polypeptide of the TGF-β superfamily is selected from the group consisting of activins, nodal, myostatin and GDF3.

4. The chemically defined medium according to claim 3, wherein the at least one polypeptide of the TGF-β superfamily is selected from activins.

5. The chemically defined medium according to claim 1, wherein the chemically defined medium is free of albumin and/or TGF-β1.

6. The chemically defined medium according to claim 1, wherein the one or more buffer components are selected from inorganic bicarbonate, inorganic phosphate or 4-(2-hydroxyethyl)-1-piperazineethanesulfonic acid (HEPES).

7. The chemically defined medium according to claim 1, wherein the concentration of selenium is in the range of 1 μg/L to 100 μg/L.

8. The chemically defined medium according to claim 1, further comprising insulin and/or transferrin, wherein the concentration of transferrin is in the range of 0.1 mg/L to 100 mg/L and/or the concentration of insulin is in the range of 0.1 mg/L to 100 mg/L.

9. The chemically defined medium according to claim 1, further comprising ascorbic acid, wherein the concentration of ascorbic acid is in the range of 3 mg/L to 300 mg/L.

10. The chemically defined medium according to claim 1, wherein one fatty acid is present at a concentration in the range of $4.6 \times 10^{-3}$ mg/L to $4.6 \times 10^{-2}$ mg/L.

11. A cell culture system, comprising human pluripotent stem cells, and a chemically defined medium according to claim 1.

12. The cell culture system according to claim 11, further comprising an extracellular matrix.

13. A method for culturing eukaryotic cells, the method comprising culturing eukaryotic cells in the chemically defined medium according to claim 1.

14. The method according to claim 13, wherein the eukaryotic cells are human pluripotent stem cells.

15. The method according to claim 13, wherein the eukaryotic cells are human induced pluripotent stem cells.

16. The method according to claim 14, wherein the culturing of human pluripotent cells is performed as an adherent cell culture.

17. The method according to claim 14, wherein the culturing of human pluripotent cells is performed on an extracellular matrix.

18. The method according to claim 14, wherein the culturing of human pluripotent cells is performed on a xeno-free extracellular matrix.

\* \* \* \* \*